US006254827B1

(12) United States Patent
Ackley et al.

(10) Patent No.: US 6,254,827 B1
(45) Date of Patent: *Jul. 3, 2001

(54) METHODS FOR FABRICATING MULTI-COMPONENT DEVICES FOR MOLECULAR BIOLOGICAL ANALYSIS AND DIAGNOSTICS

(75) Inventors: Donald E. Ackley, Cardiff; Timothy L. LeClair, San Diego; Paul D. Swanson, Santee, all of CA (US)

(73) Assignee: Nanogen, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/240,920

(22) Filed: Jan. 29, 1999

Related U.S. Application Data

(63) Continuation-in-part of application No. 09/026,618, filed on Feb. 20, 1998, now Pat. No. 6,099,803, which is a continuation-in-part of application No. 08/753,962, filed on Dec. 4, 1996, which is a continuation-in-part of application No. 08/534,454, filed on Sep. 27, 1995, now Pat. No. 5,849,486, which is a continuation-in-part of application No. 08/304,657, filed on Sep. 9, 1994, now Pat. No. 5,632,957, and a continuation of application No. 08/859,644, filed on May 20, 1997, which is a continuation-in-part of application No. 08/271,882, filed on Jul. 7, 1994, now Pat. No. 6,017,696, which is a continuation-in-part of application No. 08/146,504, filed on Nov. 1, 1993, now Pat. No. 5,605,662, and a continuation of application No. 08/725,976, filed on Oct. 4, 1996, now Pat. No. 5,929,208, and a continuation of application No. 08/709,358, filed on Sep. 6, 1996, now Pat. No. 6,129,828, and a continuation of application No. 08/677,305, filed on Jul. 9, 1996, now Pat. No. 5,965,452, and a continuation of application No. 08/846,876, filed on May 1, 1997.

(51) Int. Cl.[7] .................................................. G01N 15/06

(52) U.S. Cl. ...................... 422/68.1; 422/50; 436/283.1; 436/286.1; 436/287.1; 436/299.1
(58) Field of Search ................ 422/50, 68.1; 436/283.1, 436/286.1, 287.1, 299.1

(56) References Cited

U.S. PATENT DOCUMENTS 3,950,738    4/1976   Hayashi et al. ...................... 365/185

(List continued on next page.)

FOREIGN PATENT DOCUMENTS 0228075    7/1987   (EP).

(List continued on next page.)

OTHER PUBLICATIONS

Abrams et al. "Comprehensive Detection of Single Base Changes In Human Genomic DNA Using Denaturing Gradient Gel Electrophoresis & a GC Clamp", *Genomics*, 7, 1990, 463–475.

(List continued on next page.)

*Primary Examiner*—Ardin H. Marschel
(74) *Attorney, Agent, or Firm*—Lyon & Lyon LLP

(57) ABSTRACT

A method for manufacturing a multicomponent flip-chip device is disclosed. The device includes a chip disposed adjacent to a substrate, the substrate including a via therethrough. The device is adapted to receive a fluid to be placed on the substrate, wherein the fluid then flows through the via down to the chip. The chip includes a sealant free region and a sealant receiving region. The method includes the steps of placing a chip adjacent to a substrate. Light is exposed to the substrate and through the via, down onto the surface of the chip. A light-curable, wickable sealant is applied to the interface between the substrate and the chip, wherein the light at least partially cures the sealant to preclude the sealant from flowing to the sealant free region. Additional curing of sealant may also be performed.

24 Claims, 23 Drawing Sheets

U.S. PATENT DOCUMENTS

| | | | |
|---|---|---|---|
| 3,995,190 | 11/1976 | Salgo | 313/391 |
| 4,283,773 | 8/1981 | Daughton et al. | 364/132 |
| 4,563,419 | 1/1986 | Ranki et al. | 435/6 |
| 4,580,895 | 4/1986 | Patel | 356/39 |
| 4,584,075 | 4/1986 | Goldstein | 204/522 |
| 4,594,135 | 6/1986 | Goldstein | 204/551 |
| 4,751,177 | 6/1988 | Stabinsky | 435/6 |
| 4,787,963 | 11/1988 | MacConnell | 204/450 |
| 4,807,161 | 2/1989 | Comfort et al. | 364/550 |
| 4,816,418 | 3/1989 | Mack et al. | 436/518 |
| 4,822,566 | 4/1989 | Newman | 422/82 |
| 4,828,979 | 5/1989 | Klevan et al. | 435/6 |
| 4,908,112 | 3/1990 | Pace | 210/198 |
| 5,063,081 | 11/1991 | Cozzette et al. | 435/4 |
| 5,074,977 | 12/1991 | Cheung et al. | 205/775 |
| 5,075,077 | 12/1991 | Durley, III et al. | 422/56 |
| 5,096,669 | 3/1992 | Lauks et al. | 422/61 |
| 5,096,807 | 3/1992 | Leaback | 435/6 |
| 5,125,748 | 6/1992 | Bjornson et al. | 356/414 |
| 5,126,022 | 6/1992 | Soane et al. | 204/458 |
| 5,143,854 | 9/1992 | Pirrung et al. | 436/518 |
| 5,164,319 | 11/1992 | Hafeman et al. | 435/287 |
| 5,166,063 | 11/1992 | Johnson | 435/173 |
| 5,200,051 | 4/1993 | Cozzette et al. | 204/403 |
| 5,202,231 | 4/1993 | Drmanac et al. | 435/6 |
| 5,219,726 | 6/1993 | Evans | 435/6 |
| 5,227,265 | 7/1993 | DeBoer et al. | 430/41 |
| 5,234,566 | 8/1993 | Osman et al. | 204/403 |
| 5,242,797 | 9/1993 | HIrshfeld | 435/6 |
| 5,304,487 | 4/1994 | Wilding et al. | 435/29 |
| 5,312,527 | 5/1994 | Mikkelsen et al. | 205/777 |
| 5,338,435 | * 8/1994 | Betts et al. | 204/406 |
| 5,433,819 | 7/1995 | McMeen | 216/20 |
| 5,434,049 | 7/1995 | Okano et al. | 435/6 |
| 5,445,525 | 8/1995 | Broadbent et al. | 439/64 |
| 5,516,698 | 5/1996 | Begg et al. | 436/89 |
| 5,527,670 | 6/1996 | Stanley | 435/6 |
| 5,527,681 | 6/1996 | Holmes | 435/6 |
| 5,605,662 | 2/1997 | Heller et al. | 422/68 |
| 5,632,957 | 5/1997 | Heller et al. | 422/68 |
| 5,653,939 | 8/1997 | Hollis et al. | 422/50 |
| 5,677,195 | 10/1997 | Winkler et al. | 436/518 |
| 5,681,751 | 10/1997 | Begg et al. | 436/89 |
| 5,849,486 | 12/1998 | Heller et al. | 435/6 |

FOREIGN PATENT DOCUMENTS

| | | |
|---|---|---|
| 2156074 | 10/1985 | (GB) . |
| 2247889 | 3/1992 | (GB) . |
| WO86/03782 | 7/1986 | (WO) . |
| WO88/08528 | 11/1988 | (WO) . |
| WO89/01159 | 2/1989 | (WO) . |
| WO89/10977 | 11/1989 | (WO) . |
| WO90/01564 | 2/1990 | (WO) . |
| WO92/04470 | 3/1992 | (WO) . |
| WO93/22678 | 11/1993 | (WO) . |
| WO95/07363 | 3/1995 | (WO) . |
| WO96/01836 | 1/1996 | (WO) . |
| WO98/01758 | 1/1998 | (WO) . |
| WO98/51819 | 11/1998 | (WO) . |
| 57087 | 9/1990 | (YU) . |

OTHER PUBLICATIONS

Anand and Southern "Pulsed Field Gel Electrophoresis," *Gel Electrophoresis of Nucleic Acids—A Practical Approach*, 2d. Ed., D. Rickwood and B.D. Hames (New York:IRL Press 1990), pp 101–123.

Anderson and Young, "Quantitative Filter Hybridization," *Nucleic Acid Hybridization—A Practical Approach*, Eds. B.D. Hames and S.J. Higgins (Washington, D.C. :IRL Press 1985) pp 73–111.

Bains, "Setting a Sequence to Sequence a Sequence," *Bio/Technology*, 10:757–758 (1992).

Barinaga, "Will 'DNA Chip' Speed Genome Initiative?", *Science*, 253:1489 (1991).

Beattie et al., "Genosensor Technology," *The 1992 San Diego Conference: Genetic Recognition*, pp 1–5 (Nov., 1992).

Beltz et al., "Isolation of Multigene Families and Determination of Homologies by Filter Hybridization Methods," *Methods in Enzymology*, 100:266–285 (1983).

Brown et al. "Electrochemically Induced Adsorption of Radio–Labelled DNA on Gold and HOPG Substrates for STM Investigations", *Ultramicroscopy*, 38, 1991, 253–264.

Conner et al., "Detection of Sickle Cell $\beta^3$–Globin Allele by Hybridization With Synthetic Oligonucleotides," *Proc. Natl. Acad. Sci. USA*, 80:278–282 (1983).

Drmanac et al., "Sequencing of Megabase Plus DNA by Hybridization: Theory of the Method," *Genomics*, 4:114–128 (1989).

Drmanac et al., "DNA Sequence Determination by Hybridixation: A Strategy for Efficeint Large–Scale Sequencing," *Science*, 260: 1649–1652 (1993).

Eggers et al. "Biochip Technology Development", BioChip Technology Development, Lincoln Laboratory Technical Report 901, Nov. 9, 1990.

Fiaccabrino et al., "Array of Individually Addressable Microelectrodes", Sensors and Actuators B, 18–19 (1994) 675–677.

Fodor et al., "Multiplexed Biochemical Assays With Biological Chips," *Nature*, 364:555–556 (1993).

Fodor et al., "Light–Directed, Spatially Addressable Parallel Chemical Synthesis," *Science*, 251:767–773 (1992).

Horejsi, "Some Theoretical Aspects of Affinity Electrophoresis," *Journal of Chromatography*, 178:1–13 (1979).

Horejsi et al., Determination of Dissociation Constants of Lectin Sugar Complexes by Means of Affinity Electrophoresis, *Biochimica at Biophysica Acta*, 499:200–300 (1977).

Kakerow et al., "A Monolithic Sensor Array of Individually Addressable Microelectrodes", Sensors and Actuators A, 43 (1994) 296–301.

Mathews, Kricka. "Analytical Strategies For The Use Of DNA Probes". *Analytical Biochemistry*, 169, 1988, 1–25.

Placek. "New Trends in Electrochemical Analysis of Nucleic Acids", *Bioelectrochemistry and Bioenergetics*, 20, 1988, 179–194.

Ranki et al., "Sandwich Hybridization as a Convenient Method for the Detection of Nucleic Acids in Crude Samples,", *Gene*, 21:77–85 (1983).

Saiki, "Amplification of Genomic DNA," *PCR Protocols: A Guide to Methods and Applications*, (Academic Press, Inc. 1990), pp 13–20.

Southern et al. "Analyzing and Comparing Nucleic Acid Sequences by Hybridization to Arrays of Oligonucleotides Evaluation Using Experimental Models," *Genomics*, 13:1008–1017 (1992).

Strezoska et al., "DNA Sequencing by Hybridization: 100 Bases Read by a Non–Gel–Based Method", *Proc. Natl. Acad. Sci. USA*, 88:10089–93 (1991).

Wallace et al., "Hybridization of Synthetic Oligodexribonucleotides to $\phi$ x 174 DNA: The Effect of Single Base Pair Mismatch," *Nucleic Acid Res.*, 6:3543–3557 (1979).

Washizu, "Electrostatic Manipulataion of Biological Objects," *Journal of Electrostatics*, 25:109–123 (1990).

Washizu and Kurosawa, "Electrostatic Manipulation of DNA in Microfabricated Structures," *IEEE Transactions on Industry Applications*, 26:1165–1172 (1990).

Brown et al., "Electrochemically Induced Adsorption of Radio–Labelled DNA on Gold and HOPG Substrates for STM Investigations", *Ultramicroscopy*, 38 (1991) pp 253–264.

Palacek, "New Trends in Electrochemical Analysis of Nucleic Acids", *Bioelectrochemistry and Bioenergetics*, 20 (1988) pp 179–194.

* cited by examiner

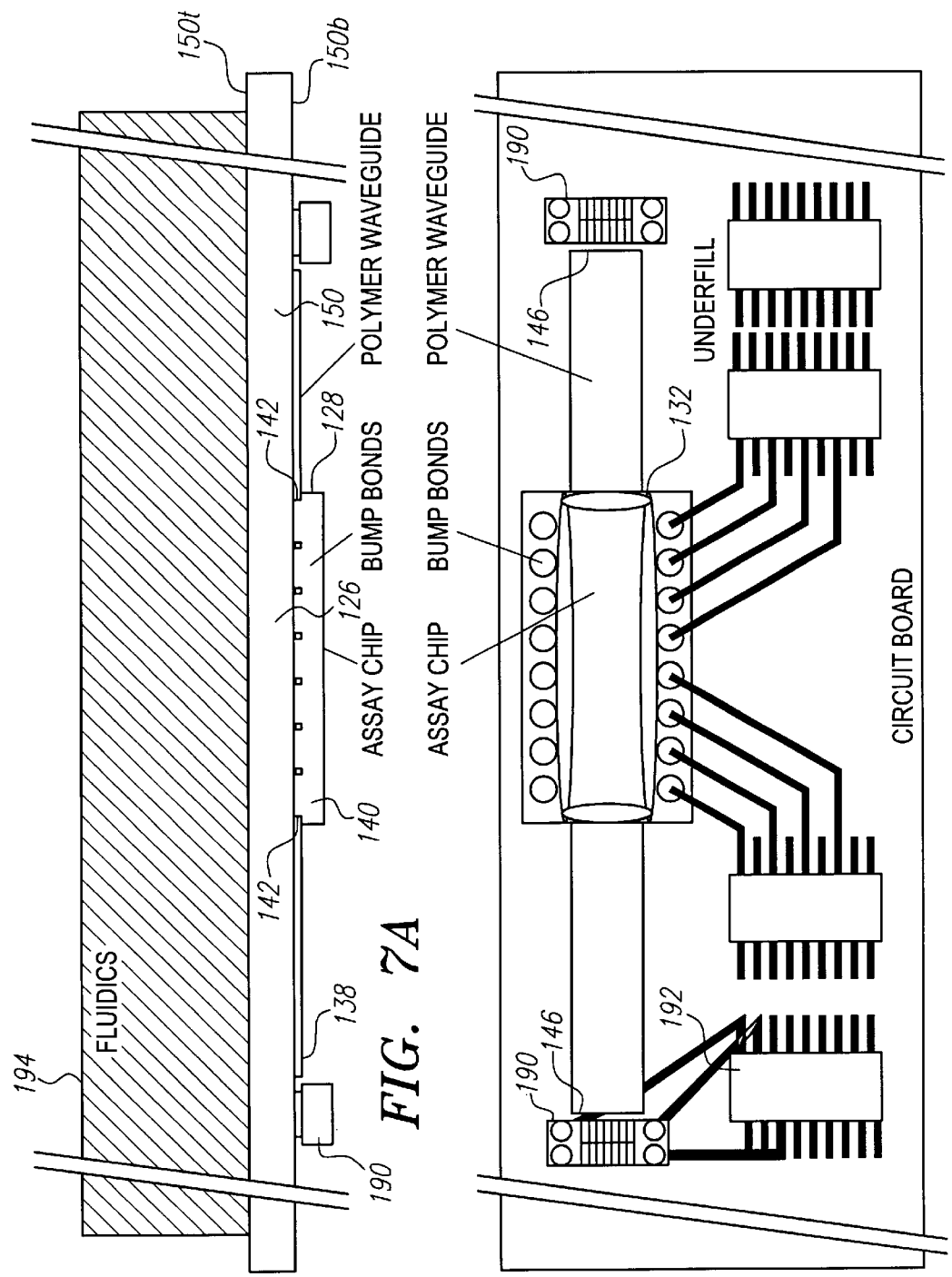

METHODS FOR FABRICATING MULTI-COMPONENT DEVICES FOR MOLECULAR BIOLOGICAL ANALYSIS AND DIAGNOSTICS

RELATED APPLICATION INFORMATION

This application is a continuation-in-part application of application Ser. No. 09/026,618, filed Feb. 20, 1998, now U.S. Pat. No. 6,099,803 entitled "Advance Active Electronic Devices for Molecular Biological Analysis and Diagnostics and Methods for Manufacture of Same", now U.S. Pat. No. 6,099,803, which is a continuation-in-part of application Ser. No. 08/753,962, filed Dec. 4, 1996, entitled "Laminated Assembly for Active Bioelectronic Devices", which is a continuation-in-part of Ser. No. 08/534,454, filed Sep. 27, 1995, entitled "Apparatus and Methods for Active Programmable Matrix Devices", now issued as U.S. Pat. No. 5,849,486, which is a continuation-in-part of application Ser. No. 08/304,657, filed Sep. 9, 1994, entitled, as amended, "Molecular Biological Diagnostic Systems Including Electrodes", now issued as U.S. Pat. No. 5,632,957, continued as Ser. No. 08/859,644, which is a continuation-in-part of application Ser. No. 08/271,882, filed Jul. 7,1994 filled May 20, 1997, entitled "Control System for Active Programmable Electronic Microbiology System" entitled, as amended, "Methods for Electronic Stringency Control for Molecular Biological Analysis and Diagnostics", now U.S. Pat. No. 6,017,696, which is a continuation-in-part of application Ser. No. 08/146,504, filed Nov. 1, 1993, entitled, as amended, "Active Programmable Electronic Devices for Molecular Biological Analysis and Diagnostics", now issued as U.S. Pat. No. 5,605,662, continued as application Ser. No. 08/725,976 filed Oct. 4, 1996, entitled "Methods for Electronic Synthesis of Polymers", now U.S. Pat. No. 5,929,208 and application Ser. No. 08/709,358, filed Sep. 6, 1996, entitled "Apparatus and Methods for Active Biological Sample Preparation"now U.S. Pat. No. 6,129,828; and is related to application Ser. No. 08/677,305, filled Jul. 9, 1996, entitled "Multiplexed Active Biological Array", now U.S. Pat. No. 5,965,452; and is also related to application Ser. No. 08/846,876, filed May 1, 1997, entitled "Scanning Optical Detection System", all incorporated herein by reference as if fully set forth herein.

This application is also related to the following applications filed on even date herewith, entitled "Advanced Active Electronic Devices Including Collection Electrodes for Molecular Biological Analysis and Diagnostics", "Multi-component Devices for Molecular Biological Analysis and Diagnostics", "Devices for Molecular Biological Analysis and Diagnostics Including Waveguides", and "Advanced Active Circuits and Devices for Molecular Biological Analysis and Diagnostics", all of which are incorporated herein by reference.

1. Field of the Invention

These invention relates to methods of manufacture and devices useful in performing active biological operations. More particularly, the inventions relate to devices and methods for manufacture of such devices containing active electrodes especially adapted for electrophoretic transport of nucleic acids, their hybridization and analysis.

2. Background of the Invention

Molecular biology comprises a wide variety of techniques for the analysis of nucleic acid and protein. Many of these techniques and procedures form the basis of clinical diagnostic assays and tests. These techniques include nucleic acid hybridization analysis, restriction enzyme analysis, genetic sequence analysis, and the separation and purification of nucleic acids and proteins (See, e. g., J. Sambrook, E. F. Fritsch, and T. Maniatis, *Molecular Cloning: A Laboratory Manual*, 2 Ed., Cold spring Harbor Laboratory Press, Cold Spring Harbor, 1989).

Most of these techniques involve carrying out numerous operations (e. g., pipetting, centrifugations, electrophoresis) on a large number of samples. They are often complex and time consuming, and generally require a high degree of accuracy. Many a technique is limited in its application by a lack of sensitivity, specificity, or reproducibility. For example, these problems have limited many diagnostic applications of nucleic acid hybridization analysis.

The complete process for carrying out a DNA hybridization analysis for a genetic or infectious disease is very involved. Broadly speaking, the complete process may be divided into a number of steps and substeps. In the case of genetic disease diagnosis, the first step involves obtaining the sample (blood or tissue). Depending on the type of sample, various pre-treatments would be carried out. The second step involves disrupting or lysing the cells, which then release the crude DNA material along with other cellular constituents. Generally, several sub-steps are necessary to remove cell debris and to purify further the crude DNA. At this point several options exist for further processing and analysis. One option involves denaturing the purified sample DNA and carrying out a direct hybridization analysis in one of many formats (dot blot, microbead, microplate, etc. ). A second option, called Southern blot hybridization, involves cleaving the DNA with restriction enzymes, separating the DNA fragments on an electrophoretic gel, blotting to a membrane filter, and then hybridizing the blot with specific DNA probe sequences. This procedure effectively reduces the complexity of the genomic DNA sample, and thereby helps to improve the hybridization specificity and sensitivity. Unfortunately, this procedure is long and arduous. A third option is to carry out the polymerase chain reaction (PCR) or other amplification procedure. The PCR procedure amplifies (increases) the number of target DNA sequences relative to non-target sequences. Amplification of target DNA helps to overcome problems related to complexity and sensitivity in genomic DNA analysis. All these procedures are time consuming, relatively complicated, and add significantly to the cost of a diagnostic test. After these sample preparation and DNA processing steps, the actual hybridization reaction is performed. Finally, detection and data analysis convert the hybridization event into an analytical result.

The steps of sample preparation and processing have typically been performed separate and apart from the other main steps of hybridization and detection and analysis. Indeed, the various substeps comprising sample preparation and DNA processing have often been performed as a discrete operation separate and apart from the other substeps. Considering these substeps in more detail, samples have been obtained through any number of means, such as obtaining of full blood, tissue, or other biological fluid sample. In the case of blood, the sample is processed to remove red blood cells and retain the desired nucleated (white) cells. This process is usually carried out by density gradient centrifugation. Cell disruption or lysis is then carried out on the nucleated cells to release DNA, preferably by the technique of sonication, freeze/thawing, or by addition of lysing reagents. Crude DNA is then separated from the cellular debris by a centrifigation step. Prior to hybridization, double-stranded DNA is denatured into single stranded form. Denaturation of the double-stranded DNA has generally been performed by the techniques involving heating (>Tm), changing salt concentration, addition of base (NaOH), or denaturing reagents (urea, formamide, etc.).

Nucleic acid hybridization analysis generally involves the detection of a very small number of specific target nucleic acids (DNA or RNA) with an excess of probe DNA, among a relatively large amount of complex non-target nucleic acids. The substeps of DNA complexity reduction in sample preparation have been utilized to help detect low copy numbers (i.e. 10,000 to 100,000) of nucleic acid targets. DNA complexity is overcome to some degree by amplification of target nucleic acid sequences using polymerase chain reaction (PCR). (See, M. A. Innis et al, *PCR Protocols: A Guide to Methods and Applications*, Academic Press, 1990). While amplification results in an enormous number of target nucleic acid sequences that improves the subsequent direct probe hybridization step, amplification involves lengthy and cumbersome procedures that typically must be performed on a stand alone basis relative to the other substeps. Substantially complicated and relatively large equipment is required to perform the amplification step.

The actual hybridization reaction represents one of the most important and central steps in the whole process. The hybridization step involves placing the prepared DNA sample in contact with a specific reporter probe, at a set of optimal conditions for hybridization to occur to the target DNA sequence. Hybridization may be performed in any one of a number of formats. For example, multiple sample nucleic acid hybridization analysis has been conducted on a variety of filter and solid support formats (See G. A. Beltz et al., in *Methods in Enzymology*, Vol. 100, Part B, R. Wu, L. Grossman, K. Moldave, Eds., Academic Press, New York, Chapter 19, pp. 266–308, 1985). One format, the so-called "dot blot" hybridization, involves the non-covalent attachment of target DNAs to filter, which are subsequently hybridized with a radioisotope labeled probe(s). "Dot blot" hybridization gained wide-spread use, and many versions were developed (see M. L. M. Anderson and B. D. Young, in *Nucleic Acid Hybridization—A Practical Approach*, B. D. Hames and S. J. Higgins, Eds., IRL Press, Washigton, D. C. Chapter 4, pp. 73–111, 1985). It has been developed for multiple analysis of genomic mutations (D. Nanibhushan and D. Rabin, in EPA 0228075, Jul. 8, 1987) and for the detection of overlapping clones and the construction of genomic maps (G. A. Evans, in U.S. Pat. No. 5,219,726, Jun. 15, 1993).

New techniques are being developed for carrying out multiple sample nucleic acid hybridization analysis on micro-formatted multiplex or matrix devices (e.g., DNA chips) (see M. Barinaga, 253 Science, pp. 1489, 1991; W. Bains, 10 Bio/Technology, pp. 757–758, 1992). These methods usually attach specific DNA sequences to very small specific areas of a solid support, such as micro-wells of a DNA chip. These hybridization formats are micro-scale versions of the conventional "dot blot" and "sandwich" hybridization systems.

The micro-formatted hybridization can be used to carry out "sequencing by hybridization"(SBH) (see M. Barinaga, 253 Science, pp. 1489, 1991; W. Bains, 10 Bio/Technology, pp. 757–758, 1992). SBH makes use of all possible n-nucleotide oligomers (n-mers) to identify n-mers in an unknown DNA sample, which are subsequently aligned by algorithm analysis to produce the DNA sequence (R. Drmanac and R. Crkvenjakov, Yugoslav Patent Application #570/87,1987; R. Drmanac et al., 4 Genomics, 114, 1989; Strezoska et al., 88 Proc. Natl. Acad. Sci. USA 10089, 1992; and R. Drmanac and R. B. Crkvenjakov, U.S. Pat. No. 5,202,231, Apr. 13, 1993).

There are two formats for carrying out SBH. The first format involves creating an array of all possible n-mers on a support, which is then hybridized with the target sequence. The second format involves attaching the target sequence to a support, which is sequentially probed with all possible n-mers. Both formats have the fundamental problems of direct probe hybridizations and additional difficulties related to multiplex hybridizations.

Southern, United Kingdom Patent Application GB 8810400, 1988; E. M. Southern et al., 13 Genomics 1008, 1992, proposed using the first format to analyze or sequence DNA. Southern identified a known single point mutation using PCR amplified genomic DNA. Southern also described a method for synthesizing an array of oligonucleotides on a solid support for SBH. However, Southern did not address how to achieve optimal stringency condition for each oligonucleotide on an array.

Concurrently, Drmanac et al., 260 Science 1649–1652, 1993, used the second format to sequence several short (116 bp) DNA sequences. Target DNAs were attached to membrane supports ("dot blot" format). Each filter was sequentially hybridized with 272 labeled 10-mer and 11-mer oligonucleotides. A wide range of stringency condition was used to achieve specific hybridization for each n-mer probe; washing times varied from 5 minutes to overnight, and temperatures from 0° C. to 16° C. Most probes required 3 hours of washing at 16° C. The filters had to be exposed for 2 to 18 hours in order to detect hybridization signals. The overall false positive hybridization rate was 5% in spite of the simple target sequences, the reduced set of oligomer probes, and the use of the most stringent conditions available.

A variety of methods exist for detection and analysis of the hybridization events. Depending on the reporter group (fluorophore, enzyme, radioisotope, etc. ) used to label the DNA probe, detection and analysis are carried out fluorimetrically, colorimetrically, or by autoradiography. By observing and measuring emitted radiation, such as fluorescent radiation or particle emission, information may be obtained about the hybridization events. Even when detection methods have very high intrinsic sensitivity, detection of hybridization events is difficult because of the background presence of non-specifically bound materials. A number of other factors also reduce the sensitivity and selectivity of DNA hybridization assays.

Attempts have been made to combine certain processing steps or substeps together. For example, various microrobotic systems have been proposed for preparing arrays of DNA probe on a support material. For example, Beattie et al., in *The 1992 San Diego Conference: Genetic Recognition*, November, 1992, used a microrobotic system to deposit micro-droplets containing specific DNA sequences into individual microfabricated sample wells on a glass substrate.

Generally, the prior art processes have been extremely labor and time intensive. For example, the PCR amplification process is time consuming and adds cost to the diagnostic assay. Multiple steps requiring human intervention either during the process or between processes is suboptimal in that there is a possibility of contamination and operator error. Further, the use of multiple machines or complicated robotic systems for performing the individual processes is often prohibitive except for the largest laboratories, both in terms of the expense and physical space requirements.

Attempts have been made to enhance the overall sample introduction, to sample preparation analysis process. Given the relatively small volume of sample material which is often times available, improved processes are desired for the efficient provisions of sample, transport of sample and effective analysis of sample. While various proposals have been advanced, certain systems enjoy relative advantages in certain circumstances.

Yet another area of interest is in the electrical addressing of relatively large arrays. As array grow relatively large, the efficient operation of the system becomes more of a consideration. Efficient interfacing of an array based system with electrical connections off-chip raise pin or contact limitation issues. Further, constraints regarding effective chip or array size present issues regarding the selection of components, and the size of them, for inclusion on the chip or substrate. Often times, various selections must be made to provide an effective optimization of advantages in the overall design.

One proposed solution for the control of an array of electrodes utilizing less than one individual dedicated connection per electrode or test site is provided in Kovacs U.S. patent application Ser. No. 08/677,305, entitled "Multiplexed Active Biological Array", filed Jul. 9, 1996, incorporated herein as if fully set forth herein. The array is formed of a plurality of electrode sites, a typical electrode site including an electrode, a driving element coupled to the electrode for applying an electrical stimulus to the electrode and a local memory coupled to the driving element for receiving and storing a signal indicative of a magnitude of the electrical stimulus to be applied to the electrode. Multiple embodiments are disclosed for selectively coupling a value signal through coaction of a row line and a column line for storage in the local memory. In this way, the values at the various electrodes in the array may differ from one another.

In Fiaccabrino, G. C., et al., "Array of Individual Addressable Microelectrodes", Sensors and Actuators B, 18–19, (1994) 675–677, an array of $n^2$ electrodes are connected to two n pins, plus 2 additional pins for signal output and bulk bias. The row and column signals drive series connected transistors to provide a single value to a working electrode. This system does not enable the switching of two or more electrodes simultaneously at different potentials.

In Kakerow, R. et al., "A Monolithic Sensor Array of Individually Addressable Microelectrodes", Sensors and Actuators A, 43 (1994) 296–301, a monolithic single chip sensor array for measuring chemical and biochemical parameters is described. A 20×20 array of individually addressable sensor cells is provided. The sensor cells are serially addressed by the sensor control unit. One horizontal and one vertical shift register control selection of the sensor cells. Only one sensor cell is selected at a time. As a result, multiple sites may not be activated simultaneously.

Yet another concern is the ability to test an electronic device prior to application of a conductive solution on the device. As devices or chips become more complicated, the possibility of a manufacturing or process error generally increases. While visual inspection of circuitry may be performed, further testing may ensure an operational device is provided to the end user.

As is apparent from the preceding discussion, numerous attempts have been made to provide effective techniques to conduct multi-step, multiplex molecular biological reactions. However, for the reasons stated above, these techniques are "piece-meal", limited and have not effectively optimized solutions. These various approaches are not easily combined to form a system which can carry out a complete DNA diagnostic assay. Despite the long-recognized need for such a system, no satisfactory solution has been proposed previously.

SUMMARY OF THE INVENTION

Methods of manufacture and apparatus adapted for advantageous use in active electronic devices utilized for biological diagnostics are disclosed. Specifically, various layouts or embodiments, including the selection of components, are utilized in advantageous combination to provide useful devices. Various structures, shapes and combinations of electrodes coact with various applied signals (voltages, currents) so as to effect useful preparation, transport, diagnosis, and analysis of biological or other electrically charged material. Various advantageous protocols are described.

In a first preferred embodiment, an electronic device for performing active biological operations comprises in combination a support substrate, an array of micro-locations disposed on the substrate, a first collection electrode disposed on the substrate, first and second focusing electrodes disposed on the substrate, the first and second electrodes being disposed at least in part adjacent the array of microlocations, the distance between the first and second electrodes adjacent the array preferably being smaller than the distance between the first and second electrodes in yet another region disposed away from the array, and counter electrodes disposed on the substrate. In one implementation, a "V" or "Y" configuration is utilized, which serves to focus charged biological material into a desired region. Preferably, the focusing electrodes have a proximal end disposed near or adjacent the array of microlocations, and a remote portion disposed away from the array. The distance between the proximal ends of the first and second electrode is less than the distance between the proximal ends of the first and second electrode.

In operation of this embodiment, a solution containing DNA or other biological material to be interrogated is provided to the device, above the substrate. As a typical initial step, the concentration electrode and return electrodes are activated so as to transport and concentrate the charged biological materials onto or near the concentration region. In the preferred embodiment, the concentration electrode and the return electrode or electrodes interrogate a relatively large volume of the sample. Typically, the collection electrode and counter electrodes are disposed on the substrate so that the electrophoretic lines of force are significant over substantially all of the flow cell volume. By way of example, the concentration and return electrodes may be disposed near the periphery of the footprint of the flow cell. In yet another embodiment, they are maybe disposed at substantially opposite ends of the flowcell. In yet another embodiment, the return electrode substantially circumscribes the footprint of the flow, with a centrally disposed collection electrode. Effective interrogation of the sample within the flow cell is one desired result. Once the sample has been concentrated, the focusing electrodes may be operated so as to funnel or further focus the materials towards the array of microlocations. As materials move from the concentration electrode towards the array, the decreasing spacing between the first and second focusing electrodes serves to concentrate the analytes and other charged material into a smaller volume. In this way, a more effective transportation of materials from a relatively larger concentration electrode region to a relatively smaller microelectrode array region may be achieved.

It yet another optional aspect of this embodiment of this invention, one or more transport electrodes are provided, the transport electrodes being disposed on the substrate, and positioned between the first collection electrode and the array. In the preferred embodiment, there are at least two transport electrodes, and further, the transport electrodes are of a different size, preferably wherein the ratio of larger to smaller is at least 2:1. In this way, the relatively large area subtended by the collection electrode may be progressively moved to smaller and smaller locations near the analytical region of the device. This arrangement both aids in transitioning from the relatively large area of the collection electrode, but the stepped nature of the embodiment reduces current density mismatches. By utilizing a stepped, preferably monotonically stepped size reduction, more effective transportation and reduced burnout are achieved.

In yet another embodiment of device, an electronic device for performing biological operations comprises a support substrate, an array of microlocations disposed on the substrate, the array being formed within a region, the region including a first side and an opposite side, a first collection electrode disposed on the substrate adjacent the array, and a second collection electrode disposed on the substrate, adjacent the array, the first and second collection electrodes being at least in part on the opposite side of the region. In the preferred embodiment, the collection electrodes have an area at least 80% of the area of the region of the array. In this way, the sample may be collected in a relatively large area adjacent the region containing microlocations, from which the DNA or other charged biological materials may be provided to the region.

In one method for use of this device, the collection electrode may first collect the materials, and then be placed repulsive relative to the collected material, thereby sweeping the material towards the region containing the array. The material may be transported in a wave manner over the array, permitting either interaction with a passive array or an electrically active array. Alternatively, the material may be moved over the region of the array, and effective maintained in that position by application of AC fields. This embodiment has proved capable of performance of repeat hybridizations, where material is move to and interacted with the array, after which it is moved out of the region, and preferably held by the collection electrode or on another electrode, after which it is moved to the array for a second, though possibly different, interaction.

In yet another embodiment of device design, a substantially concentric ring design is utilized. In combination, an electronic device for performing active biological operations includes a support substrate, an array of microlocations disposed on the substrate in a annular region, a first counter electrode disposed on the substrate surrounding the array, and a collection electrode disposed on the substrate and disposed interior of the array. In the preferred embodiment, the first counter or return electrode is segmented, optionally having pathways resulting in the segmentation which serve as pathways for electrical connection to the array. In yet another variation of this embodiment, multiple rings are provided surrounding the array.

In yet another embodiment of this invention, a reduced component count, preferably five component, system is implemented in a flip-chip arrangement for providing active biological diagnostics. The device comprises in combination a support substrate having first and second surfaces and a via, pathway or hole between the first and second surfaces to permit fluid flow through the substrate, at least one of the first and second surfaces supporting electrical traces, a second substrate including at least a first surface, the first surface being adapted to be disposed in facing arrangement with at least one of the first and second surfaces of the first substrate and positioned near, e.g., under, the via, the second substrate including electrically conductive traces connecting to an array of microlocations, the array being adapted to receive said fluid through the via, pathway or hole, electrically conductive interconnects, e.g., bumps, interconnecting the electrical traces on the second surface of the support substrate and the electrical traces on the first surface of the second substrate, a sealant disposed between the second face of the support substrate and the first face of the second substrate, said sealant providing a fluidic seal by and between the first substrate and the second substrate, and optionally, a flowcell dispose on the first surface of the first substrate. Preferably, the structures utilize a flip-chip arrangement, with the diagnostic chip below the support substrate in operational orientation. This design is particularly advantageous in reducing the number of components in the device, and to improve manufacturing reliability.

In yet another embodiment, an electronic device for performing active biological operations comprises a support substrate having a first and second surface, and a via between the first and second surfaces to permit fluid flow through the substrate, a second substrate including at least a first surface, the first surface being adapted to be disposed in facing arrangement with the second surface of the first substrate, the second substrate including an array of microlocations, the array being adapted to receive said fluid, a sealant disposed between the second face of the support substrate and the first face of the second substrate, a source of illumination, and a waveguide having an input adapted to receive the illumination from the source, and an output adapted to direct the illumination to the array, the waveguide being substantially parallel to the support substrate, the illumination from the waveguide illuminating the array. In the preferred embodiment, the source of illumination is a laser, such as a laser bar. Such a device may utilize a support substrate which is flex circuit or a circuit board.

A novel, advantageous method of manufacture may be utilized with some or all of the embodiments. The method is particularly advantageous for the manufacture of the flip-chip design. In that structure, there is a chip disposed adjacent a substrate, the substrate including a via therethrough, the structure being adapted to receive a fluid to be placed on the substrate, and to flow through the via down to the chip, where at least a portion of the chip includes an area to be free of sealant overcoat. Selection of sealant viscosity and materials may effectively result in effective coverage, good thermal contact between the substrate and the chip, and fluidic sealing. In the most preferred embodiment, the method may include use of a light-curable sealant which is cured with light during application. Specifically, light is exposed to the device onto the substrate and through the via, down to the chip. Next, a light curable, wickable sealant is applied to the interface between the substrate and the chip. The light at least partially cures the sealant as a result of the exposure, whereby the sealant is precluded from flowing to said area to be free of sealant. Finally, if desired, the cure of the sealant may be completed, such as by heat treatment.

In yet another embodiment, a system or chip includes a multi-site array with electrically repetitive unit cell locations. Typically, the array is formed of rows and columns, most typically an equal number of rows and columns. The individual unit cells of the array of unit cells is selected by action of selectors such as one or more row selectors and one or more column selectors. The selector may be a memory, such as a shift register memory, or a decoder, or a combination of both. An input for address information receives addresses, typically from off-chip, though on-chip address generators may be utilized. In the preferred embodiment, the row selectors comprise shift registers, either in a by one configuration, or in a wider configuration, such as a by four configuration. In operation, the selection registers are sequentially loaded with values indicating the selection or non-selection of a unit cell, and optionally, the value (or indicator of value) of output for that cell. Optionally, memory may be provided to retain those values so as to continue the output from the unit cell.

The system or chip provides for the selective provision of current and voltage in an active biological matrix device which is adapted to receive a conductive solution including charged biological materials. In one aspect, an array of unit cells is provided. Each unit cell typically includes a row contact and a column contact. Row lines are disposed within the array, the row lines being coupled to the row contacts of the unit cell. A row selector selectively provides a row select voltage to the row lines. Further, column lines are disposed within the array, the column lines being coupled to the column contacts of the array. A column selector selectively provides a column select signal to the column lines. The unit cells are coupled to a supply voltage and to an electrode, the row select signal and the column select signal serving to select a variable current output from the electrode of the unit cell. A return electrode is coupled to a potential and adapted to contact the conductive solution. In operation, selective activation of one or more unit cells results in the provision of current within the conductive solution.

In one preferred embodiment of a unit cell, a symmetric arrangement is utilized. A first column select unit, preferably a transistor, and a first row select unit, also preferably a transistor, are in series relation between a first source, e.g., voltage and/or current source, and a node, typically a current output node. In the preferred embodiment, the column select transistor may be precisely controlled under application of a gate voltage such as from the column shift register memory. Preferably, the select units may differ from each other in their controllability, such as by varying the channel length in the control transistor. The channel lengths have been chosen so as to match the gain or other desired properties between the row and column transistors. Also, the long channel length provides the ability to control small currents with reasonable control signals. Thus, by application of potentials from the row selector and column selector, application of potential to the control gates results in output of current at the unit cell.

The unit cell circuit preferably further includes a second column select unit, preferably a transistor, and a second row select unit, also preferably a transistor, used in series relation between a second source, e.g., voltage and/or current source, and a node, typically the previously referred to node, i.e., a current output node. In the preferred embodiment, the first source is a supply potential Vcc and the second source is a reference potential, such as ground. Preferably the nodes are the same node, such that there is a series connection between Vcc and ground of the first column select unit and first row select unit, the node, and the second row select unit and the second column select unit. Optionally, the return electrode is biased at a potential between the potential of the first source and the second source, e.g., Vcc/2.

In yet another aspect of the preferred embodiment, test circuitry is included. Test circuitry may be utilized to ensure circuit continuity, by permitting testing prior to application of a fluidic solution. A first test transistor spans the first column select and first row select transistor. Likewise, a second test transistor spans the second column select and second row select transistor. Selective activation ensures continuity of the circuit. Alternatively, the test circuit function may be performed by special programming of the row and column transistors, e.g., turning on of the first and second row select and first and second column select transistors.

In yet a further aspect of this invention, the current supply to the test site is varied. Examples of the variation of current over time may include static direct current (i.e., no variation as a function of time), square wave, sinusoidal, sawtooth, or any waveform which varies with time. In one embodiment, the currents, whether static or varying as a function of time, are supplied to the column selection circuitry, which are then selectively provided in a digital manner to the column lines for coupling to the selected electrodes. This mixed analog and digital technique permits significant control of the values and waveforms of the current supplied at the individual electrodes. The waveforms, e.g., the current waveforms, may be generated either on-chip or off-chip. Additionally, control or operation of the overall circuitry, and/or generation of signals such as the current waveforms may be generated through the use of digital to analog converters (DACs), central processing units (CPUs), through the use of local memory for storage of values, through the use of clock generators for timing and control of various waveforms, and through the use of digital signal processors (DSPs).

In one aspect of this invention, a system based upon current control of a first current is utilized to effect control of a second current. Preferably, a current mirror arrangement is utilized. A current supply provides a variable value of current for use in a voltage generation circuit. In the preferred embodiment, multiple current sources are utilized, being summed at their output, under the selective control of a memory for selective inclusion. A variable voltage is generated at a node, preferably through use of a voltage divider circuit which receives the output of the variable current. The variable voltage at the node is coupled to a control element in the unit cell, the control element preferably providing a variable resistance between a first voltage and an output node. The variable control element thereby provides a variable current output. In this way, a first current of a relatively higher value may be utilized to control a second current of a relatively smaller value, the second current being supplied in operation to the conductive solution applied to the active electronic device for purposes of molecular biological analysis and diagnostics. In one embodiment, a reduction of current by a factor of 32 permits provision of currents to the device which are easily generated and controlled, yet results in currents of a magnitude which are required for effective operation of the active biological device.

In yet another aspect of these inventions, the various devices may be decorated or covered with various capture sequences. Such capture sequences may be relatively short, such as where the collection electrode is a complexity reduction electrode. Further, relatively longer capture sequences may be used when further specificity or selectivity is desired. These capture sequences may preferably be included on the collection electrodes, or intermediate transportation electrodes.

Accordingly, it is an object of this invention to provide an active biological device having reduced costs of manufacture yet consistent with achieving a small size microlocation.

It is yet another object of this invention to provide devices which provide increased functionality.

It is yet a further object of this invention to provide devices which achieve a high degree of functionality and operability with fewer parts than known to the prior art.

It is yet a further object of this invention to provide devices which are easier to manufacture relative to the prior art.

It is yet a further object of this invention to provide circuitry and systems which eliminate or reduce the pin limitation or pin out limitations.

It is yet a further object of this invention to provide a system which provides for precise current control in an active electronic device adapted for molecular biological analysis and diagnostics, which may interface with larger currents generated by a control system.

BRIEF DESCRIPTION OF THE DRAWINGS

FIGS. 7A and 7B shows side and plan views, respectively, of an edge illuminated system in one embodiment of this invention.

DETAILED DESCRIPTION OF THE INVENTION

Figure 1A:
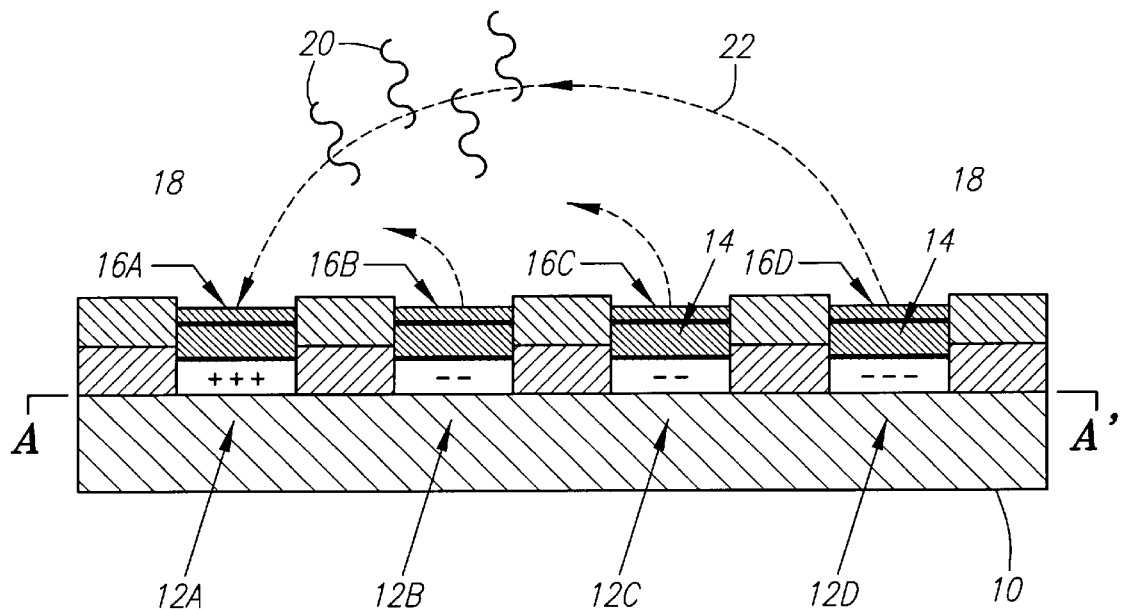
FIGS. 1A and 1B show an active, programmable electronic matrix device (APEX) in cross-section (FIG. 1A) and in perspective view (FIG. 1B).
Figure 1B:
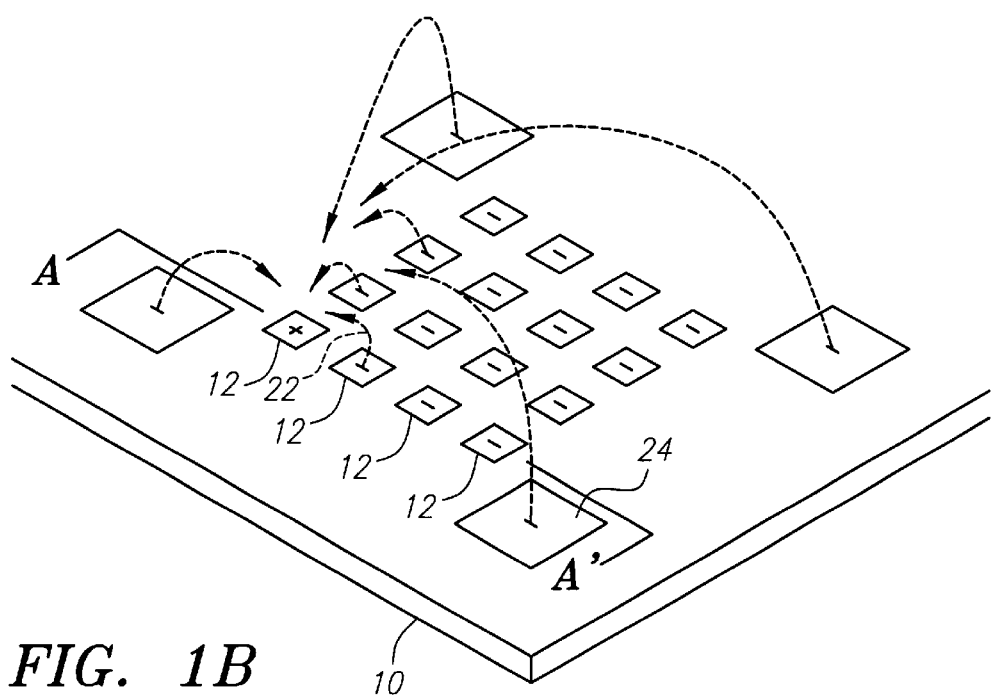

FIGS. 1A and 1B illustrate a simplified version of the active programmable electronic matrix (APEX) hybridization system for use with this invention. FIG. 1B is a perspective view, and FIG. 1A is a cross-sectional view taken in FIG. 1B at cut A–A'. Generally, a substrate 10 supports a matrix or array of electronically addressable microlocations 12. For ease of explanation, the various microlocations have been labeled 12A, 12B, 12C and 12D. A permeation layer 14 is disposed above the individual electrodes 12. The permeation layer permits transport of relatively small charged entities through it, but reduces or limits the mobility of large charged entities, such as DNA, to preferably keep the large charged entities from easily contacting the electrodes 12 directly during the duration of the test. The permeation layer 14 reduces the electrochemical degradation which would occur in the DNA by direct contact with the electrodes 12, possibly due, in part, to extreme pH resulting from the electrolytic reaction. It further serves to minimize the strong, non-specific adsorption of DNA to electrodes. Attachment regions 16 are disposed upon the permeation layer 14 and provide for specific binding sites for target materials. The attachment regions 16 have been labeled 16A, 16B, 16C and 16D to correspond with the identification of the electrodes 12A–D, respectively. The attachment regions 16 may be effectively incorporated into or integrated with the permeation layers (e.g., 12A), such as by including attachment material directly within the permeation material.

In operation, reservoir 18 comprises that space above the attachment regions 16 that contains the desired, as well as undesired, materials for detection, analysis or use. Charged entities 20, such as charged DNA are located within the reservoir 18. In one aspect of this invention, the active, programmable, matrix system comprises a method for transporting the charged material 20 to any of the specific microlocations 12. When activated, a microlocation 12 generates the free field electrophoretic transport of any charged functionalized specific binding entity 20 towards the electrode 12. For example, if the electrode 12A were made positive and the electrode 12D negative, electrophoretic lines of force 22 would run between the electrodes 12A and 12D. The lines of electrophoretic force 22 cause transport of charged binding entities 20 that have a net negative charge toward the positive electrode 12A. Charged materials 20 having a net positive charge move under the electrophoretic force toward the negatively charged electrode 12D. When the net negatively charged binding entity 20 that has been functionalized contacts the attachment layer 16A as a result of its movement under the electrophoretic force, the functionalized specific binding entity 20 becomes covalently attached to the attachment layer 16A. Optionally, electrodes 24 may be disposed outside of the array. The electrodes 24 may optionally serve as return electrodes, counter electrodes, disposal (dump) electrodes or otherwise. Optionally, a flowcell may be provided adjacent the device for fluidic containment.

Figure 2:
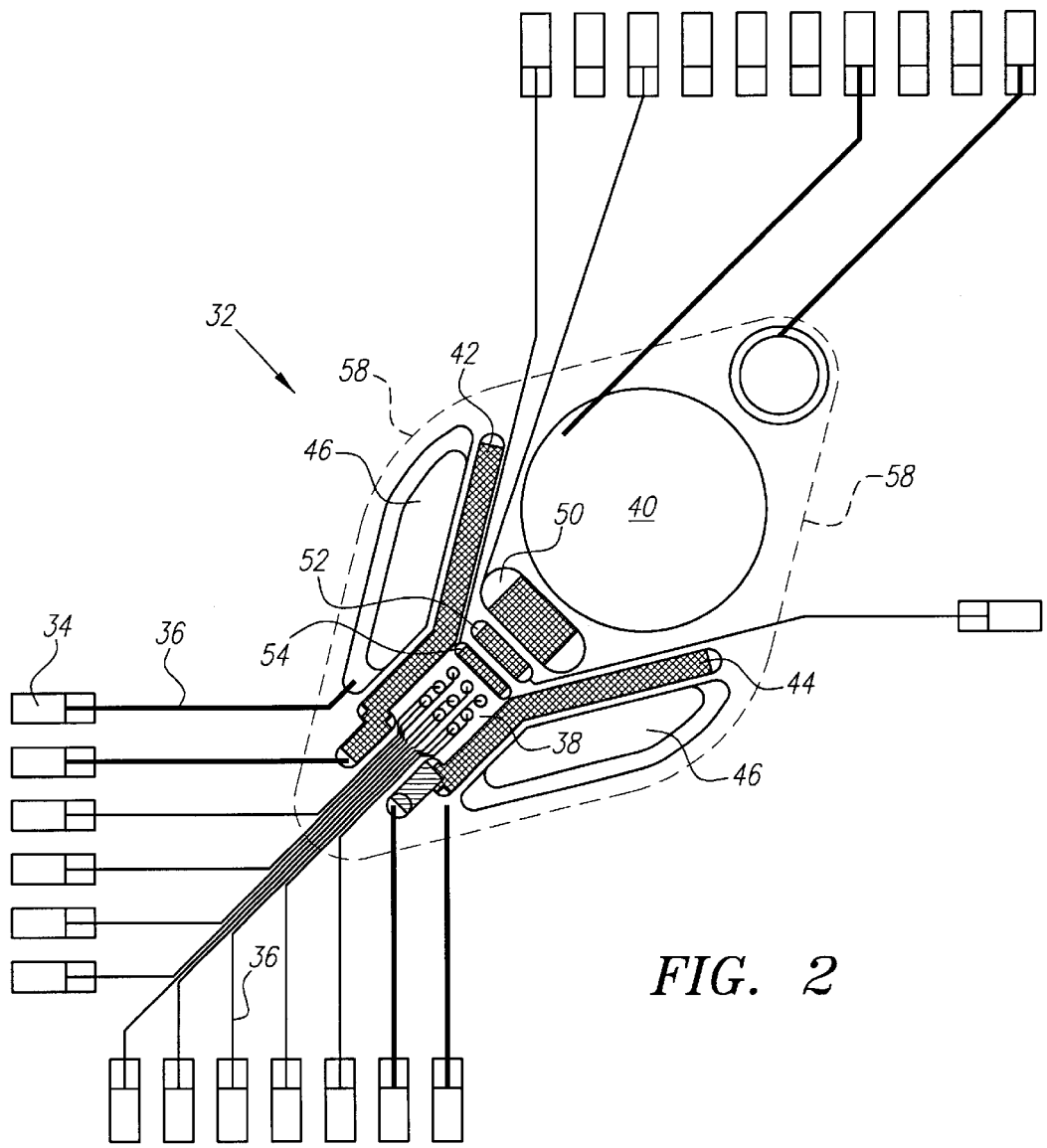
FIG. 2 is a plan view of an embodiment of the invention which utilizes varying sized electrode regions and focusing electrodes, variously referred to as the bug chip.

FIG. 2 is a plan view of one embodiment of the invention which utilizes focusing electrodes 42, 44, and optionally, transport electrodes 50, 52, 54. The device 20 includes a substrate 32, which may be of any sufficiently rigid, substantially non-conductive material to support the components formed thereon. The substrate 32 may be flex circuit (e.g., a polyimide such as DuPont Kapton, polyester, ABS or other such materials), a printed circuit board or a semiconductive material, preferably with an insulative overcoating. Connectors 34 couple to traces 36, which in turn, couple to other electrical components of the system. These components may be any form of conductor, such as copper, or gold, or any other conductor known to those skilled in the art. Various of the connectors 34 are shown unconnected to traces 36 or other electrical components. It will be appreciated by those skilled in the art that not every connector 34, such as in a system adapted to mate with an edge connector system will be utliized. Additionally, traces 36 may be of differing widths depending upon the demands, especially the current demands, to be made on that trace 36. Thus, some traces 36 may be wider, such as those being coupled to the focusing electrodes 42, 44, in comparison to those traces 36 coupled to the microlocations within the array 38. Array 38 is preferably of the form described in connection with FIGS. 1A and 1B.

A first collection electrode 40 and counter electrodes 46 are disposed on the substrate 32. These components generally fit within the footprint (shown in dashed line) of the flow cell 58, and comprise a relatively large percentage thereof, preferably at least substantially 40%, and more preferably substantially 50%, and most preferably substantially 60%. The counter electrodes 46 (sometimes functioning as return electrodes) and collection electrode 40 are preferably disposed at or near the periphery of the flow cell footprint 58, and may substantially circumscribe, e.g., to 80%, the footprint perimeter.

Typically, the collection electrode 40 and counter electrodes 46 are disposed on the substrate 32 so that the electrophoretic lines of force are significant over substantially all, e.g., 80% or more, of the flow cell volume. By way of example, the concentration 40 and counter electrodes 46 may be disposed near the periphery of the footprint 58 of the flow cell. In yet another embodiment, they may be disposed at substantially opposite ends of the flowcell footprint 58 (See, e.g., FIG. 3). In yet another embodiment, the counter-electrode substantially circumscribes the footprint of the flow, with a centrally disposed collection electrode (See, e.g., FIG. 4). The relatively large percent of coverage of the flow cell footprint 58 and its position aids in effective electrophoretic interrogation of the flow cell contents.

Returning to FIG. 2, focusing electrodes 42, 44 are disposed on the substrate 32 to aid in focusing materials collected on the collection electrode 40 to the array 38. The focusing electrodes 42, 44 are preferably disposed in a mirror-image, "Y" or "V" shaped pattern, the open end encompassing, at least in part, the collection electrode 40. As shown, there are two symmetric focusing electrodes 42, 44. One focusing electrode may be utilized, or more than two focusing electrodes may be utilized. As shown, the focusing electrodes 42, 44 include substantially parallel portions (adjacent the array) and angled portions (adjacent the transport electrodes 50, 52, 54, and optionally, the collection electrode 40) extending in a symmetrical manner enveloping the transport electrodes 50, 52, 54. Stated otherwise, there are first and second electrodes being disposed at least in part adjacent the array of microlocations, the distance between the first and second electrodes adjacent the array being smaller than the distance between the first and second electrodes in yet another region disposed away from the array. The focusing electrodes 42, 44 may optionally include portions which are disposed on the opposite side of the array 38 from the collection electrode 40. The focusing electrodes 42, 44 are preferably coupled to leads 36 which are relatively larger than the leads 36 coupled to the array 38, so as to permit the carrying of effective currents and potentials.

Transport electrodes 50, 52, 54 are optionally included. Electrodes of monotonically decreasing size as they approach the array 38 are shown. A first transport electrode 50 is relatively smaller than the collection electrode 40, the second transport electrode 52 is relatively smaller than the first transport electrode 50, and the third transport electrode 54 is yet smaller still. The differential sizing serves to reduce current density mismatches between locations, and aids in reducing or eliminating burn-out which may result if too great a current density mismatch exists. Transport efficiently is maximized. The ratio of sizes of larger to smaller is preferably substantially 2 to 1, more preferably 3 to 1, and may be even greater, such as 4 to 1 or higher.

One field-shaping protocol is as follows:

| Negative Bias | Positive Bias | Current | Bias Time |
|---|---|---|---|
| Counter Electrodes 46 | 1st Collection Electrode 40 | 75 μA | 30 sec. |
| Focusing Electrodes 42, 44 (−0.2 μA) 1st Collection Electrode 40 | 1st Transport Electrode 50 | 25 μA | 90 sec. |
| Focusing Electrodes 42, 44 (−0.2 μA) 1st Transport Electrode 50 | 2nd Transport Electrode 52 | 5 μA | 180 sec. |
| Focusing Electrodes 42, 44 (−0.2 μA) 1st Transport Electrode 50 2nd Transport Electrode 52 | 3rd Transport Electrode 54 | 3 μA | 420 sec. |
| Focusing Electrodes 42, 44 (−0.2 μA) 2nd Transport Electrode 52 | Row 3 | 1.5 μA (500 nA/pad) | 120 sec. |

-continued

| Negative Bias | Positive Bias | Current | Bias Time |
|---|---|---|---|
| 3rd Transport Electrode 54 | | | |
| Focusing Electrodes 42, 44 (−0.2 µA) | Row 2 | 1.5 µA | 120 sec. |
| 2nd Transport Electrode 52 | | (500 nA/pad) | |
| 3rd Transport Electrode 54 | | | |
| Focusing Electrodes 42, 44 (−0.2 µA) | Row 1 | 1.5 µA | 120 sec. |
| 2nd Transport Electrode 52 | | (500 nA/pad) | |
| 3rd Transport Electrode 54 | | | |

The seven steps of the field shaping protocol serve to effectively interrogate the sample volume and to correct materials onto the array 38 for analysis. In the first step, interrogation of the sample volume is effected through negative bias of the counter electrodes 46 and positive bias of the first collection electrode 40. The placement of the counterelectrodes 46 and collection electrode 40 generally near the periphery of the footprint of the flow cell 58 permit the rapid, effective interrogation of that sample volume. Secondly, with the collected material adjacent the collection 40, that electrode is made negative (repulsive) to materials of interest, while the first transport electrode 50 is made positive (attractive). The repulsion and attraction effects transport of materials from the collection electrode 40 to the first transport electrode 50. Additionally, the focusing electrodes 42, 44 are biased negative. Such a negative (repulsive) bias serves to provide a force which may be lateral to the direction of transport, thereby more centrally concentrating material in the solution. Thirdly, with material collected at the first transport electrode 50, that electrode may be biased negative (repulsive), while the second transport electrode 52 is biased positive (attractive). The focusing electrodes 42, 44 may be biased negatively, which serves to provide a repulsive force on the charged materials, thereby providing a transverse component to their direction of motion and collecting the material within a smaller physical region or volume. Fourth, the second transport electrode 52 may be biased negative, as well as optionally biasing of the first transport electrode 50, to effect transport away from those electrodes and to the now positively biased third transport electrode 54. Again, the focusing electrodes 42, 44 may retain their negative bias. The next three steps are optionally separated, as described, to transport materials to various rows or regions of the array 38.

The field shaping protocol includes currents and biased times. In this embodiment, there is an inversely proportional relationship between the size of the electrode and the amount of current supplied to it. Further, for the collection electrode 40 and transport electrodes 50, 52 and 54, there is an inversely proportional relationship between the electrode size and the bias time, that is, the smaller the electrode, the larger the bias time. Through this protocol, the current density at various devices is kept relatively more uniform, optionally substantially similar to each other. Further, as the current from a given electrode decreases (relative to a larger electrode) a relatively longer bias time may be required in order to provide transport of effective amounts of charged material between the various electrodes. Stated otherwise, for a given amount of charged material, a relatively longer bias time may be required to effect transport of a given amount of material at a lower current.

Figure 3:
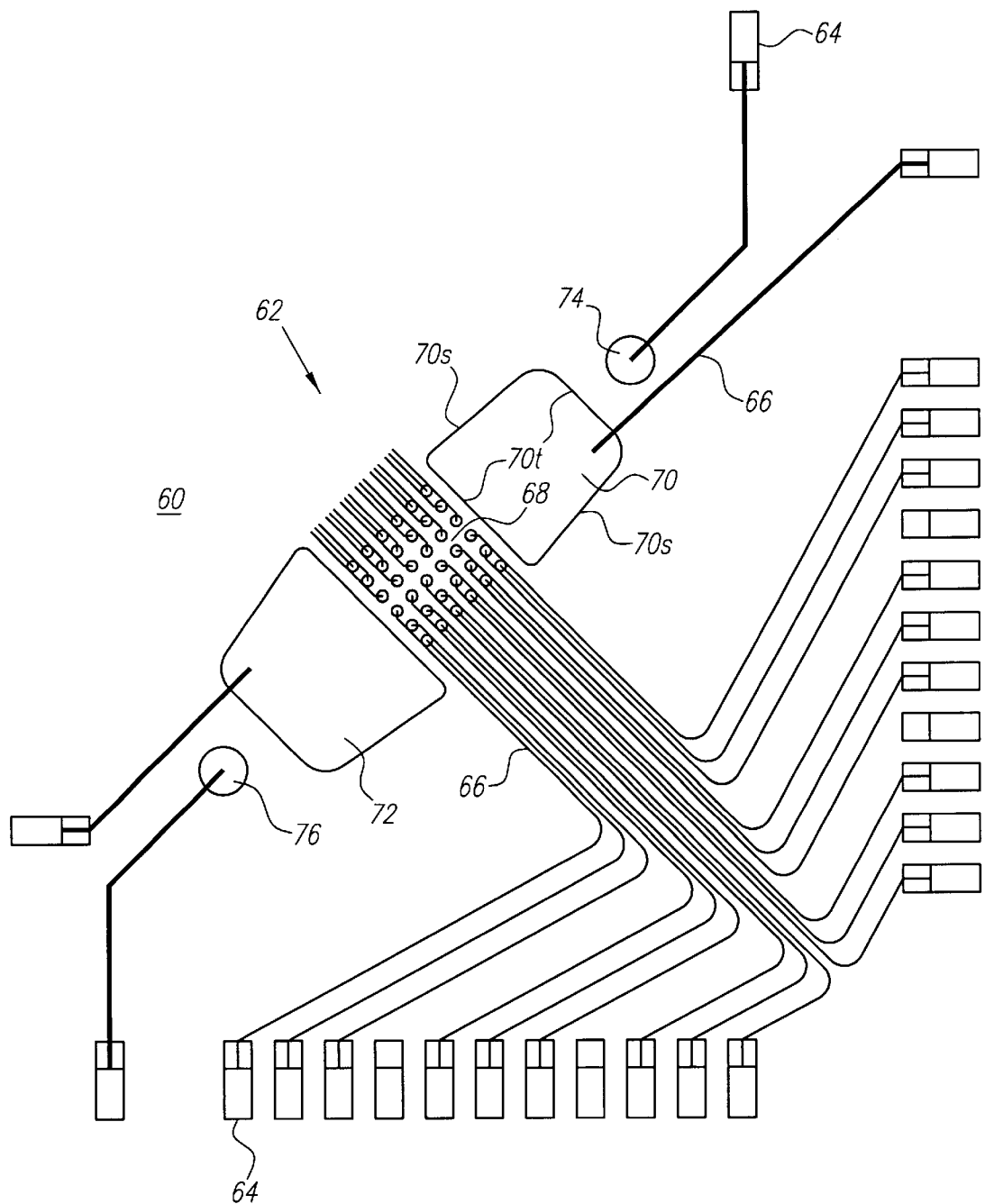
FIG. 3 is a plan view of an embodiment of the invention which utilizes a concentration electrode and paired return electrode, which is especially useful in methods which effectively transport charged biological material in a wave or sweeping motion across microlocations.

FIG. 3 is a plan view of another embodiment of this invention. As with FIG. 2, a device 60 includes a substrate 62, connectors 64, traces 66 and an array of microlocations 68. The comments made for FIG. 2 and others apply to corresponding structures in other figures. Further, the traces 66 leading from the upper left portion of the array 68 have been truncated for drawing simplicity. A corresponding arrangement to those shown in the lower right of the drawing would apply. The traces 66 may be of the same width or of varying width, such as where a relatively wider trace 66 may be utilized for larger current carrying capacity (e.g., traces 66 to first collection electrode 70 and second collection electrode 72.

FIG. 3 departs from FIG. 2 in the inclusion of a first collection electrode 70, being disposed at least in part adjacent the array 68. In the embodiment of FIG. 3, first collection electrode 70 is a trapezoid, which has a long base 70b adjacent to and parallel to one side of the array 68 and top 70t, which is preferably shorter than the base 70b, with sloping sides 70s, tapering wider (away from each other) toward the base 70b. The second collection electrode 72 is disposed on the other side of the array 68, and is similarly (though not necessarily identically) shaped and sized. Top 72t is preferably shorter than base 72b, and accordingly, the sides 72s are non-parallel and slope away from each other, moving towards the array 68. Optionally, the electrodes 70, 72 may be of different sizes, such as where the area of the first collection electrode 70 is approximately 10% smaller (optionally approximately 20% smaller) than the second collection electrode 72. Input port electrode 74 and port electrode 76 are optionally included on the substrate 62, within the footprint of the flow cell 78. The input port electrodes 74 and port electrode 76 are either of the same size or of different size.

In operation, the flow cell contents are interrogated by placing or biasing one of the first and second collection electrodes 70, 72 attractive (typically positive) to the materials to be collected. Once collected, the materials may be transported away from the first collection electrode 70 towards the array 68. The materials may be effectively held in place over the array 68, such as by application of AC fields such as at a frequency in the range from 0.01 to $10^6$ Hz, most preferably between 0.1 to $10^3$ Hz between the electrodes 70, 72. Then materials may be transported to the other electrode 70, 72 or may be repeatedly reacted by moving materials from the array 68 to the electrodes 70, 72. Optionally, the microlocations of the array 68 may be electrically active or passive.

Figure 4:
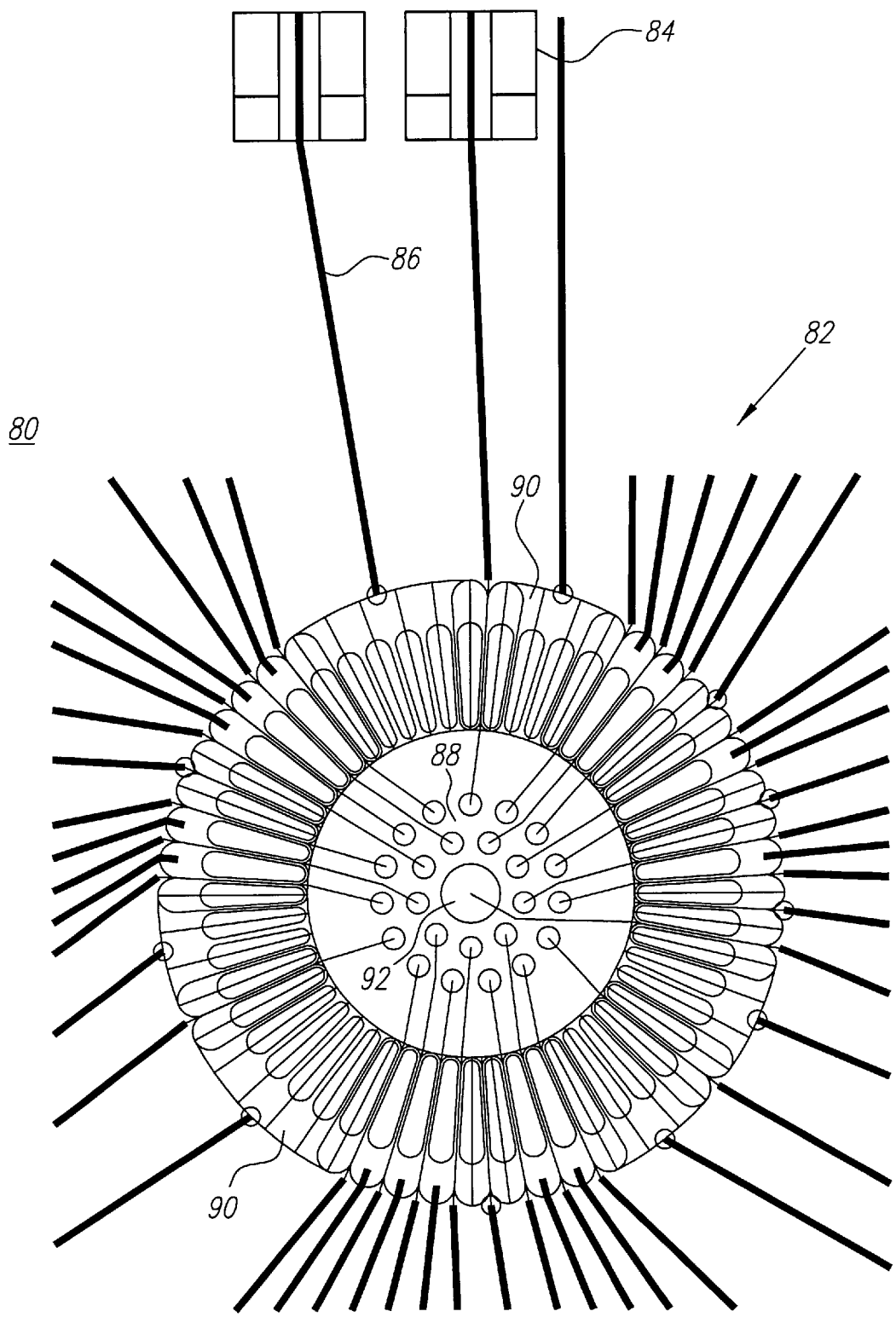
FIG. 4 is a plan view of an embodiment of the invention which utilizes a substantially circular arrangement, with a substantially centrally disposed concentration electrode.

FIG. 4 is a plan view of a concentric ring electrode embodiment. The device 80, substrate 82, connectors 84, traces 86 and array 88 are as previously described, with the exception that the array 88 may be arranged concentrically. A concentric return electrode 90 and central concentration electrode 92, preferably round, coact to concentrate material at electrode 92, and then to move it over or position it above the array 92. As with the preceding FIGS. 2 and 3, the traces have been shown in a truncated manner.

In the embodiments of FIGS. 2, 3 and 4, capture sequences or probes may be disposed on the devices. Preferably these are at least on the collection or concentration electrodes. Optionally, different sequences are disposed on different devices such as the transport electrode 50, 52 and 54 of FIG. 2. For example, each sequence as an approach is made to the array may be more specific.

Figure 5A:
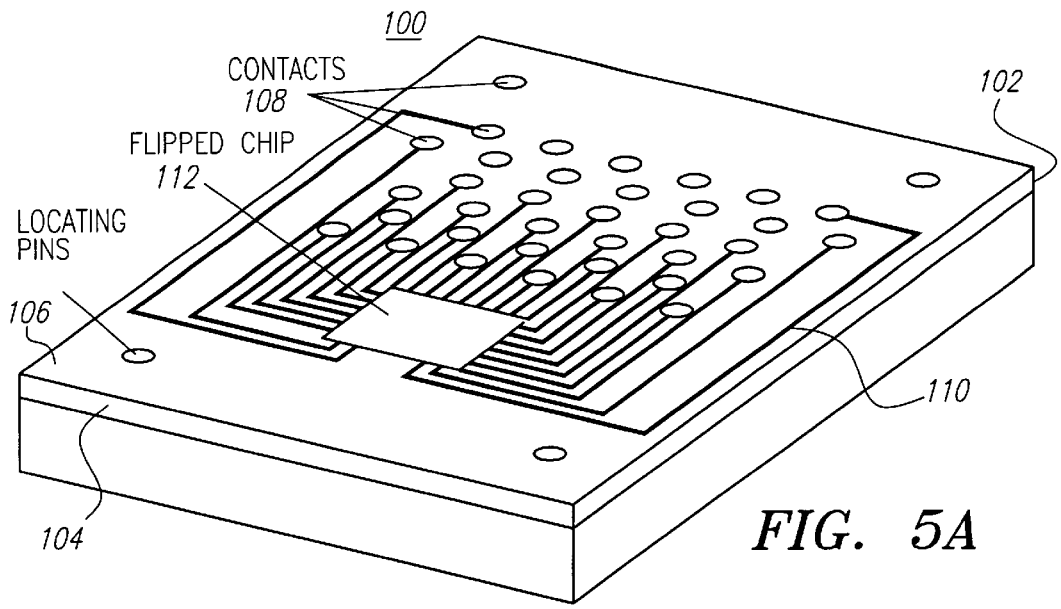
FIGS. 5A, 5B and 5C show perspective views
Figure 5B:
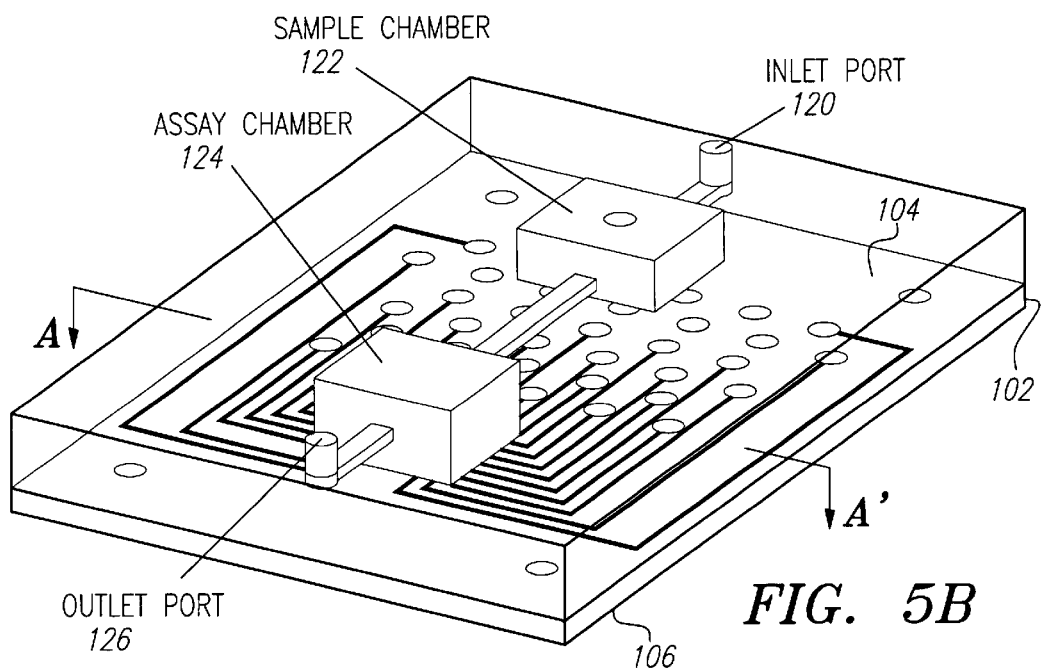
Figure 5C:
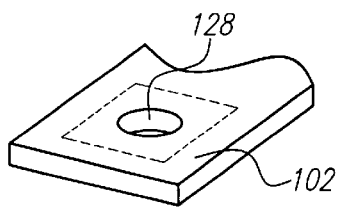
Figure 5D:
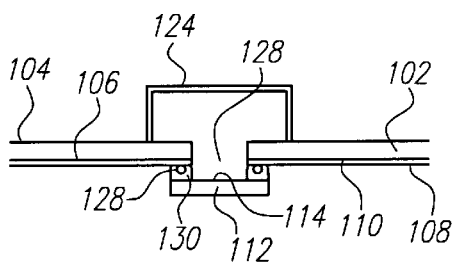
FIG. 5D shows a cross-sectional view of a flip-chip system, FIG. 5A showing the underside of the system, FIG. 5B showing a perspective view of top of the flip-chip structure including sample chamber, FIG. 5C showing a top perspective detail of the via, and FIG. 5D showing a cross-sectional view of the flowcell.

FIGS. 5A, 5B, 5C and 5D show views of the bottom, the top, the top with via 109 exposed, and a side view of the system through cut A–A' in FIG. 5B, respectively, of a flip-chip system. A device 100 includes a support substrate 102 having a first surface 104 (optionally called the top surface) and a second surface 106 (optionally called the bottom surface), which may be of materials suitable for the function of support and conduction, such as flex circuitry, printed circuit board, semiconductive material or like material. Contacts 108 lead to traces 10, which lead to the second substrate 112. This second substrate 112 may also be referred to as the flipped chip. This second substrate 112 may optionally be a chip, system or support on which assays or other diagnostic materials are provided. Contacts, such as bump contacts, e.g., solder bumps, indium solder bumps, conductive polymers, or silver filled epoxy, provide electrical contact between traces 110 and the chip or substrate 112. A sealant is disposed between the second (bottom) surface 106 of the support substrate 102 and the first (top) surface 114 of the second substrate 112. Generally, the opposing faces of the support substrate 102 and second substrate 112 are those which are placed in fluid-blocking contact via the inclusion of a sealant. An inlet port 120 may be in conductive relation to a sample chamber 122, which yet further leads to the assay chamber 124, and on to the outlet port 126. FIG. 5C shows a perspective view of the support 102 and the via 128 formed through it. As shown, the lateral width of the via 128 is less than the lateral width of the second substrate 112. The second substrate 112 is shown in dashed lines, which is disposed below the substrate 102 in the view of FIG. 5C.

In the preferred embodiment, the device 100 is formed of a minimum number of components to reduce cost, improve manufacturing simplicity and reliability or the like. One embodiment is achieved in substantially five components. While the device may be fabricated with five components, the addition of components which do not detract from or vary the inventive concept may be utilized. These components are as follows. First a support substrate 102 having a first surface 104 and second surface 106, and avia 128 between the first surface 104 and second surface 106 to permit fluid flow through the substrate 102, the second surface 106 supporting electrical traces. Second, a second substrate 112 including at least a first surface 114, the first surface being adapted to be disposed in facing arrangement with the second surface 106 of the first substrate, the second substrate 112 including electrically conductive traces connecting to an array of microlocations (See, FIG. 1A and 1B), the array being adapted to receive said fluid through the via 128. Third, electrically conductive bumps 128 interconnecting the electrical traces on the second surface of the support substrate and the electrical traces on the first surface 106 of the second substrate. Fourth, a sealant 130 disposed between the second face 106 of the support substrate 102 and the first face 114 of the second substrate 112, said sealant 130 providing a fluidic seal by and between the first substrate 102 and the second substrate 112. Fifth, a flowcell is optionally disposed on the first surface 104 of the first substrate 102. While the number of elements may vary, advantages may be obtained from selection of these five elements.

In operation, a sample is provided to the inlet port 120 and passed to the sample chamber 122. The sample chamber 122 may serve to house various sample processing functions, including but not limited to cell separation, cell lysing, cell component separation, complexity reduction, amplification (e.g., PCR, LCR, enzymatic techniques), and/or denaturation). Thereafter, the sample flows to the assay chamber 124. Solution containing sample flows down through via 128 (which is obscured in FIG. 5B by assay chamber 124, though may be seen in FIG. 5C and 5D). A space is formed comprising the via 128, bounded on the bottom by the second substrate 112, with sealant or adhesive 130 forming a barrier between the interface of the second surface 106 of the support substrate 102 and the first surface 114 of second substrate 112.

Figure 8:
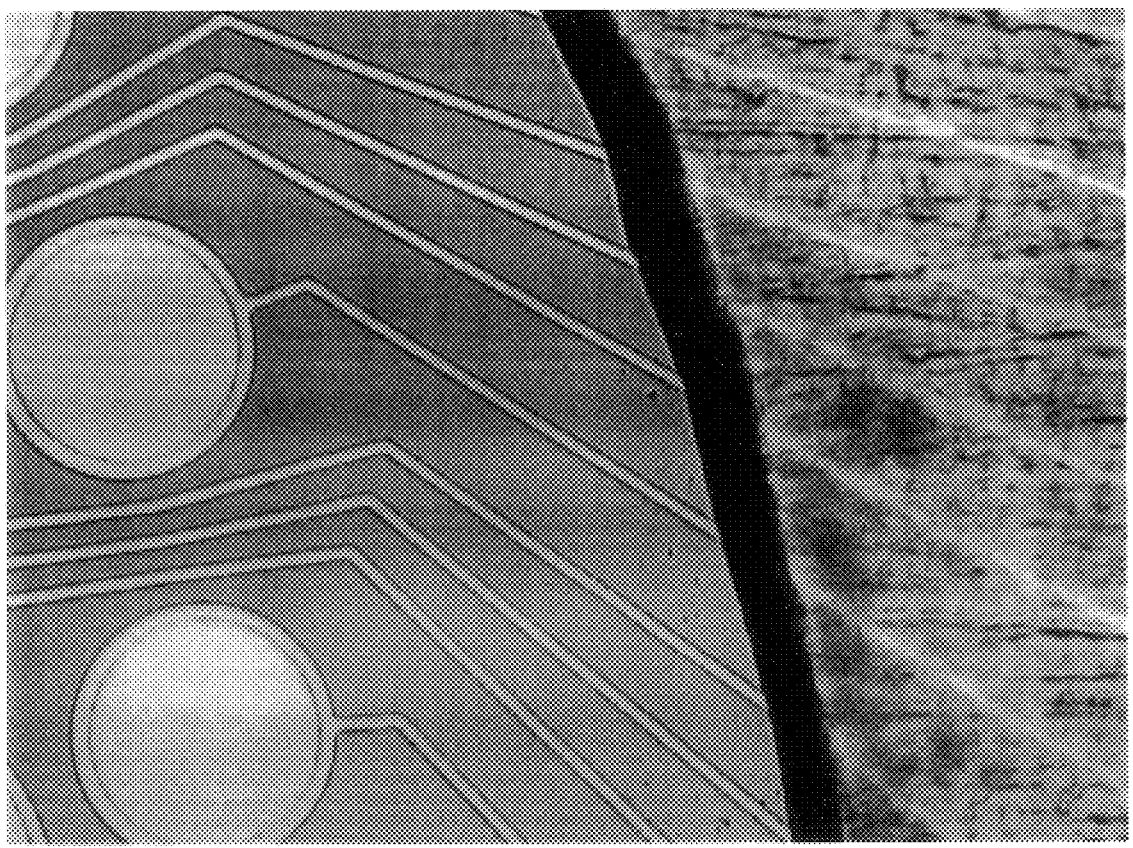
FIG. 8 is a microphotograph of barrier wall for the Norland 83H dam using a 1300 J/s fiber bundle source shadow masked with the flex circuit (Flex polyimide removed).

In the preferred method of manufacture, a light curable sealant is wicked or otherwise provided to the interface between the second surface 106 of the support substrate 102 and the first surface 114 of the second substrate. Light is provided through the via 128. A dam is formed, stopping the advance of the sealant, thereby maintaining the array, e.g., 18, substantially free from sealant or adhesive. (See FIG. 8 for a microphotograph showing the sealant free area of the array, the cured leading edge of the dam and sealant on the exterior portions of the device.) By the appropriate sizing of the lateral width of the via 128, the via 128 serves essentially as a shadow mask for the incident light, which serves to cure the sealant. Alternatively, the sealant may be supplied to the interface between the second surface 106 of the support substrate 102 and the first surface 114 of the second substrate 112 in an amount and with a viscosity such that it does not flow onto the array 18. Further or final curing of the sealant may be performed as required, such as by heating.

Figure 6A:
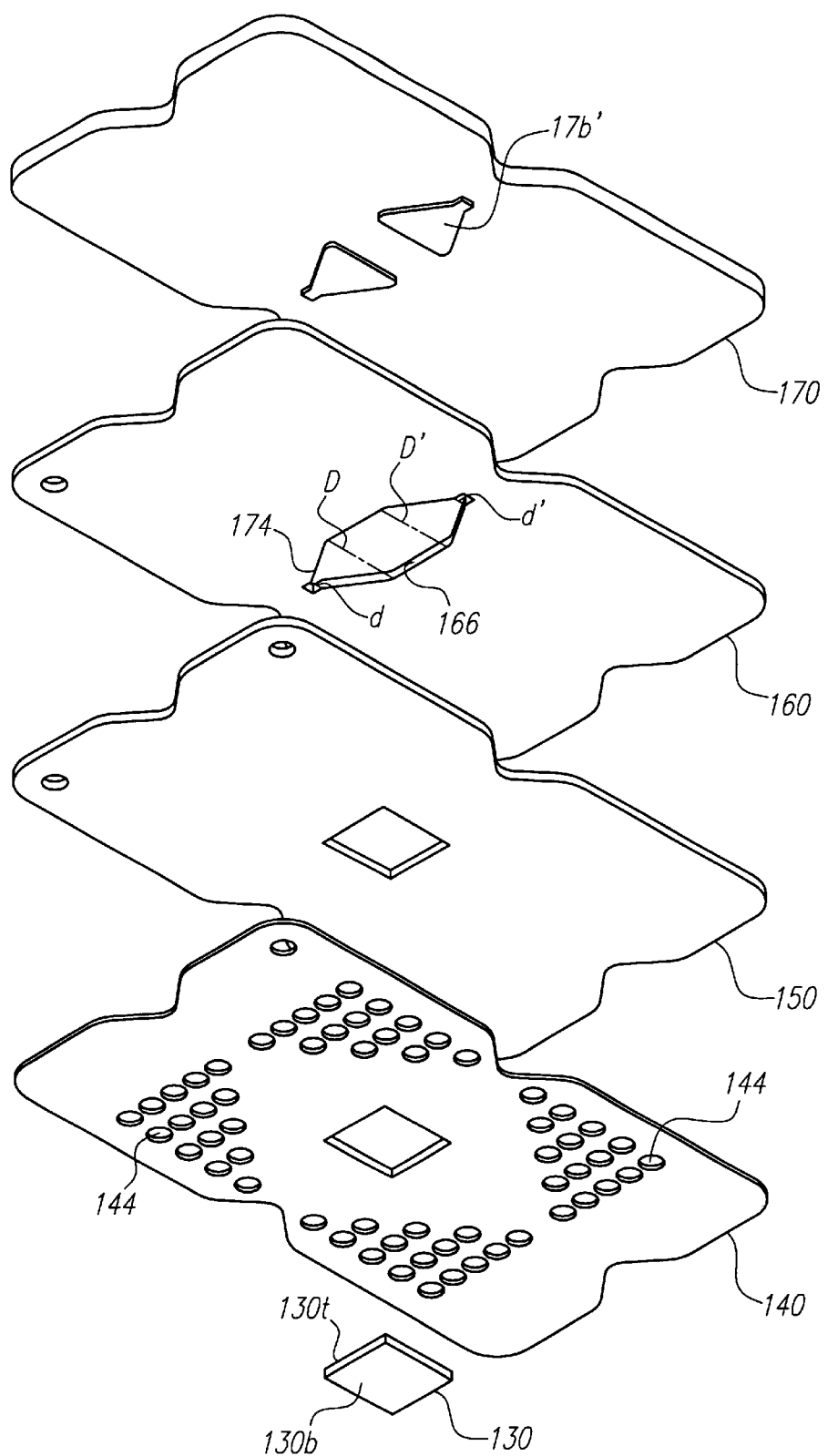
FIGS. 6A and 6B show perspective and cross-sectional views, respectively, of a flip-chip system in one embodiment.
Figure 6B:
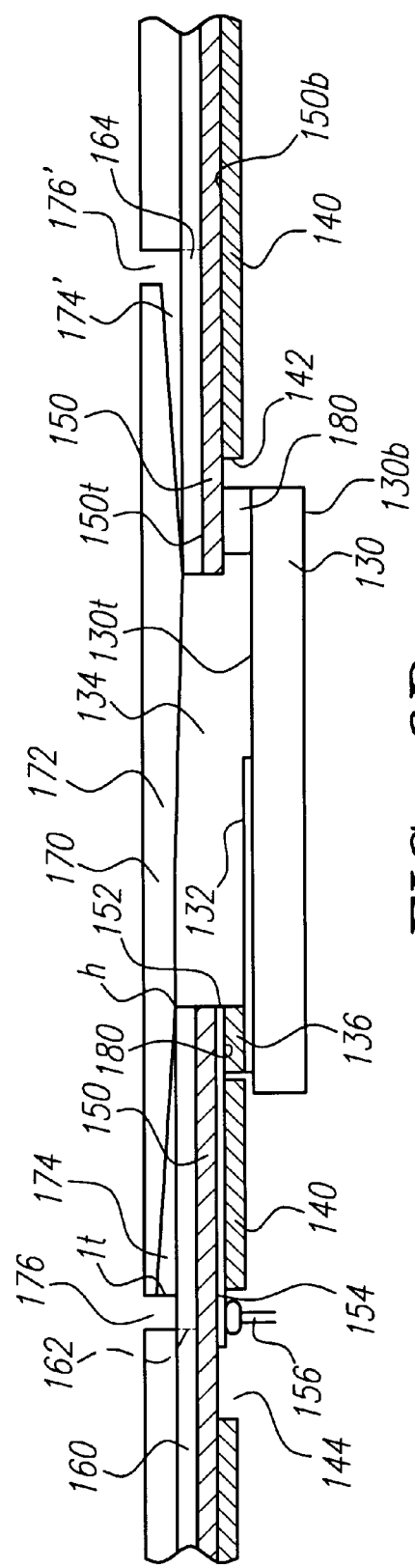

FIG. 6A shows a perspective exploded drawing and FIG. 6B shows a cross-sectional view, respectively, of a flip-chip system in accordance with one implementation of this invention. The system of FIGS. 6A and 6B include an edge illumination member 140, unique sample chamber 134 design, and a 'butterfly' input and output chamber design as compared to FIGS. 5A, 5B and 5C. A chip or substrate 130 has a first surface 130$t$ and a second surface 130$b$, at least the first surface 130$t$ including electrical regions or traces 132 thereon or therein. While the embodiment shown in cross-section in FIG. 6B shows the trace 132 disposed on the top surface 132 of the chip or substrate 130, the electrical regions may be contained wholly or partially within the chip or substrate 130, such as through the provision of semiconductive regions. These semiconductive regions may be controlled in an active manner so as to provide selective connections within the chip or substrate 130. Typically, the first surface 130$t$ is that surface on which the active biological interactions will take place. Optionally, an edge illumination member 140 may be disposed adjacent to and substantially coplanar with the first surface 130$t$ of the chip or substrate 130. The illumination sheet 140 preferably includes holes, vias or pathways 144 to permit electrical interconnections 156 to pass therethrough. As can be seen, the illumination sheet 140 may be disposed directly over conductive traces 132 or may be directly affixed to the adjacent supporting sheet 150. Electrical traces 132 may be included on the first surface 130$t$ of the substrate or chip 130. An electrically conductive element 136, such as a solder connection, indium bump, conductive polymer or the like couples the conductive pathway 132 on the substrate 130 to the conductive portion of the contact trace 154. The contact trace preferably is then contacted by a conductive member 156, such as a wire, whisker wire, or other electrical contact, for connection to the remainder of the circuit. Sealant 180 is preferably disposed between the substrate or chip 130 and the next layer 150, such as the flex support layer.

In FIG. 6B, the drawing has been presented with a conductive member 136 on the left hand side, but with sealant 180 on the right hand side. It will be appreciated that other conductive members 136, not disposed in the plane of the cut, are included and provide further mechanical support between the substrate 130 and the trace support layer 150. Further, the edge illumination layer 140 includes a terminal edge 142, which is disposed toward the upper surface 130t of the substrate or chip 130. The edge illumination layer 140 may terminate outside of or inside of the sealant 180. An adhesive layer 160 is disposed adjacent the trace support layer 150, and provides adhesive contact to an upper layer 170. The upper layer 170 may optionally include pathways, indentations, or other cutouts, such as shown for an inlet 176 and an outlet 176'. As shown, the adhesive layer 160 may optionally be a die-cutable adhesive material, such as one which includes release paper on both the top surface and the bottom surface prior to assembly. Suppliers of such materials include 3M or Dupont. As shown in FIG. 6A, the die-cutable adhesive material 160 may be cut so as to form all or a part of the wall 162, 164 of a chamber. As shown, the geometry may be made in any desired shape or flow cell configuration.

Preferably, a top member 170 is provided. As shown, the top member 170 may extend substantially over the remainder of the device. Optionally, the top member 170 may form a window 172 or other containment surface at the top of the flow cell chamber. Preferably, the top material is formed from polycarbonate or polystyrene. In the configuration of FIGS. 6A and 6B, it is typically contemplated that the array of test sites will be accessed optically through the top member 172, and accordingly, it is desirable to form the top member from materials which are substantially transparent to both the excitation and emission radiation.

FIGS. 6A and 6B show one geometry for a flow cell. In this 'butterfly' configuration, the inlet 176 is connected to a first expanding region 174 wherein the sidewalls of the chamber start at a first dimension d and expand, preferably monotonically, and most preferably linearly, to a dimension D at a point closer to the flow cell chamber 134. The flow cell chamber 134 region is characterized by substantially parallel sidewalls 166. Preferably, a first decreasing width region is provided between the flow cell region and the output. Most preferably, the decreasing region begins with a width D', most preferably where D'=D, and decreases to a width d', preferably where d'=d. As can be seen in FIGS. 6A and 6B, the height of the inlet chamber 174 decreases from the inlet at a height H to a lesser height h at the inlet to the flow cell chamber. Preferably, the decrease is monotonic, and most preferably, linear.

In the preferred embodiment, the height h of the inlet chamber and the width w are chosen such that a substantially constant flow area is provided, that is, the product of the height h and the width w (h×w) is substantially constant. Thus, as shown in the combined view of FIGS. 6A and 6B, at the portion of the inlet chamber adjacent the inlet, while the height h is relative large, the width w is relatively small. Correspondingly, when proceeding through the inlet chamber towards the flow cell chamber, as the width w increases, the height h decreases. Preferably, the outlet chamber includes substantially the same geometry, and preferably the same flow cell area constant.

FIGS. 7A and 7B are cross-sectional and plan views, respectively, of an edge illuminated, flip-chip system in accordance with one embodiment of the invention. To the extent possible, a consistent numbering of elements from FIGS. 6A and 6B will be utilized. A support substrate 150 is generally planar, and includes a first face 150t and a second face 150b. A via 126 (shown in dashed lines for the cross-section) permits fluid or solution flow from above the support substrate 150 to the second substrate 130, particularly to the first surface 130t of the second substrate 130. Sealant 180 is provided between the second face 150b of the support substrate 150 and the second substrate 130. The sealant 180 provides a preferably fluid tight-seal, so as to permit fluid flow to the array on the second substrate 130. A source of illumination 190, such as a laser bar, illuminate the array on the second substrate 130. Preferably, the system includes a waveguide 140 with an input 146 adapted to receive illumination from the source 190, and to provide illumination via output 142. The waveguide 140 is preferably co-planar with the support substrate 150, and may be secured to it, such as by being adhered to the second surface 150b of the support substrate 150. Electronics 192 may be included to control the system. Optionally, surface mounted electronic components may be included on the substrates 130, 150. Fluidics 194 may be provided in combination with the system to aid in provision of the sample to the second substrate 130.

Figure 9:
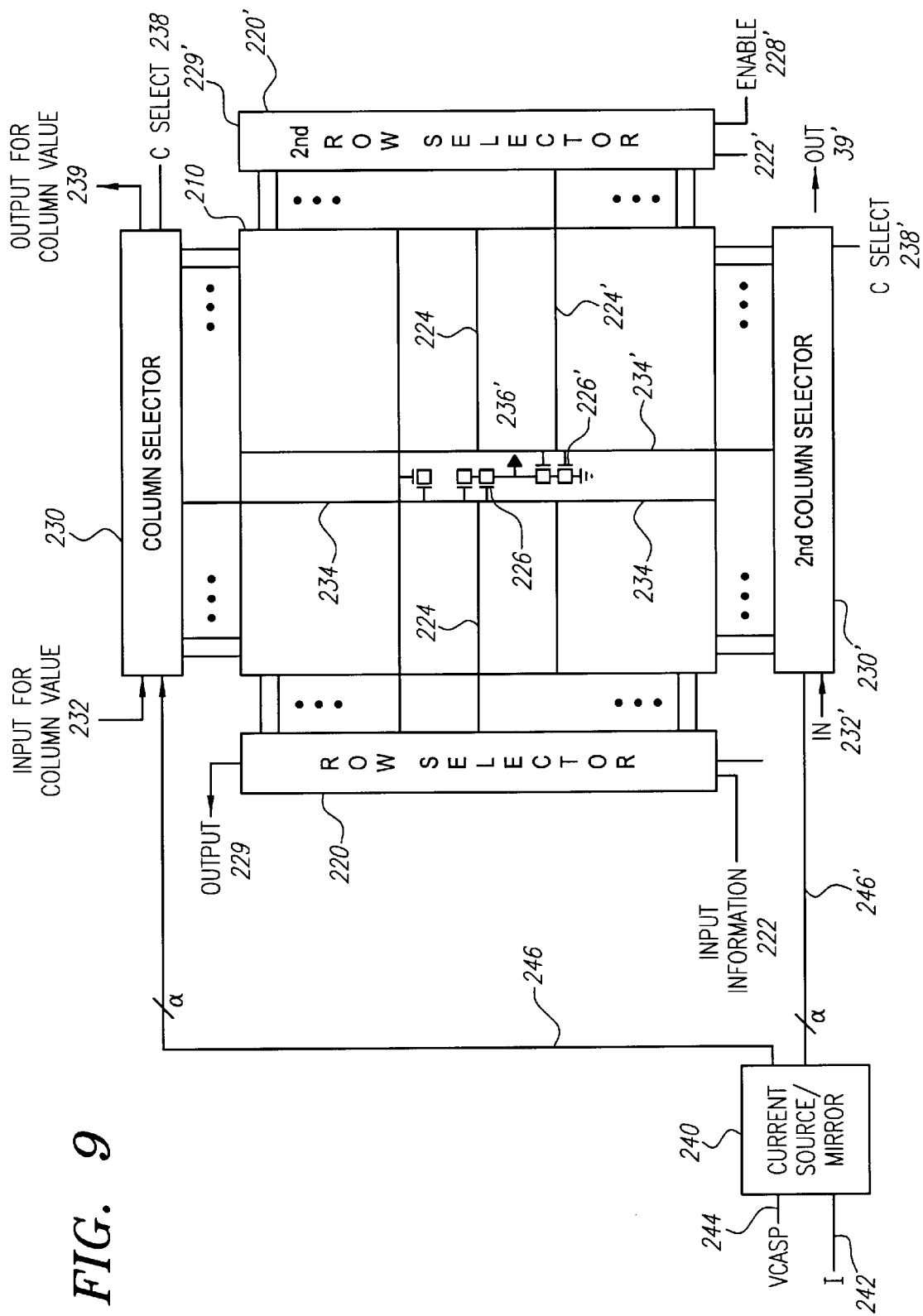
FIG. 9 is a block diagram drawing of a multiple unit cell array system.

FIG. 9 is a block diagrammatic depiction of a multiple unit cell array. In the preferred embodiment, a system or chip includes a multi-site array 210 with electrically repetitive site cell locations. Typically, the array is formed of rows and columns, more typically an equal number of rows and columns, yet most typically in an orthogonal arrangement for rows and columns. For example, an array of 10×10, 20×20 or more may be formed with these techniques. The individual unit cell 212 of the array 210 of unit cells is selected by action of selectors such as a row selector 220 and a column selector 230. The selectors 220, 230 may be a memory, such as a shift register memory, or a decoder, or a combination of both. An input for address information receives addresses, typically from off-chip, though on chip address generators may be utilized. In the preferred embodiment, the row selectors 220 comprise shift registers, either in a by one configuration (×1), or in a wider configuration, such as a by four configuration (×4). In operation, the selection registers are sequentially loaded with values indicating selection, or not, of a unit cell 212, and optionally, the value of output for that cell. Optionally, memory may be provided to retain those values so as to continue the output from the unit cell.

Considering FIG. 9 in more detail, an array 210 includes a plurality of unit cells 212. In the preferred embodiment, the unit cells 212 are arranged in rows and columns, the designation row in FIG. 9 depicting a horizontal arrangement relative to the text, and a column designating a vertical arrangement relative to the text (though it will be understood by those skilled in the art that the designations row and column may be reversed). The designation row or column may also refer to a group or subset of unit cells 212, such as a portion of a row or column, or a group or set of unit cells 212 which are not linearly contiguous. In general, there are m rows and n columns of unit cells 212, typically where m=n, and m=2, 3, 4 . . . By way of example, a 5×5 matrix of unit cells 212, a 10×10 matrix of unit cells 212 and a 20×20 matrix of unit cells 212 provides for a total number of unit cells of 25, 100 and 400, respectively.

In FIG. 9, various levels of complexity of unit cell 212 are shown. The uppermost depicted unit cell 212 is depicted as a single block-diagram unit, whereas the unit cell 212 disposed central to the figure is shown in greater complexity, akin to the structure disclosed and described in more detail in FIG. 10. It will be understood that these alternatives are depicted for expository convenience and variety, and that in a typical implementation, the construction of the individual unit cells 212 will be the same for a given device.

The unit cells 212 are addressed by action of at least one row selector 220 and at least one column selector 230. This detailed description begins with the case of a single row selector 220 and column selector 230, and later describes the use of additional selectors 220', 230'. Row selector 220 receives input information 222 and outputs a row selection signal 294 (see FIG. 10A) on one or more row lines 224. The selection signal on the row line 224 is supplied to the unit cell 212, and interacts therewith such as through a row contact 226. As drawn, a portion of row line 224 is shown disposed to the left and a portion shown drawn to the right of the unit cell 212 centrally disposed in the array 210. In typical implementation, the row line 224 will be electrically continuous, though may be made of any combination of materials. For example, the row line may be one continuous conductive line, such as formed of conductive polysilicon, or may be a combination structure such as where conductive segments are electrically connected via a higher conductivity material, such as metal, such as aluminum.

The column selector 230 receives an input 232 for determining the selection of a column, or in the preferred embodiment, the value (or correlated value) of the output at the unit cell 212. The column selector 230 is coupled to the column lines 234 which serves to provide a column select signal 296a–d to the unit cells 212. In the preferred embodiment, the column selector 230 selects more than two states (e.g., four states 296a–296d), preferably voltage states, which are supplied via the column line 234 to the unit cell 212. The column line 234 is coupled to the unit cell 212, such as through a column contact 236. In the preferred embodiment, the column contact may be a control gate for a transistor, such as a field effect transistor. (See, e.g., FIGS. 11 and 12).

If required for activation of the unit cell 212, a second row selector 220', input lines 222', second row lines 224' and column contacts 226' may be included. Likewise, a second column selector 230' may be added, having an input 232', and being coupled to secondary or supplemental column lines 234' which in turn are coupled to secondary column contacts 236'.

As shown, the row selectors 220, 220' and column selectors 230, 230' optionally include an enable input 228, 228' or chip select 238, 238'. One of the functions of these signals is to permit entry of input information 222, 222', 232, 232' without the activation of a row line 224, 224', or column line 234, 234'. Further, some or all of the row selectors 220, 220' and column selectors 220, 220' and column selectors 230, 230' may include an output 229, 229', 239, 239' which may be used for output of information. In one application, the output value may be a signal or bit, such as the most significant bit of a series, indicating that the input data has been successfully loaded into the row selector, 220, 220' or column selector 230, 230'. Optionally, this output information may be utilized to then trigger the enable or chip select signals 228, 228', 238, 238'.

Within the level of detail of FIG. 9, the row selectors 220, 220' and column selectors 230, 230' function to receive row and column input information 222, 222', 232, 232' and to use that to select one or more unit cells 212, and optionally, to provide signal values indicative of the level of current (potential) to be provided from the unit cell 212. The selectors 220, 220', 230, 230' may be in the form of memory, such as in the form of a shift register memory (See FIGS. 15 and 16 for detail), or may be in the form of a decoder circuit, such as where the desired addresses are provided as input information and the output is then in a decoded relationship thereto. Numerous circuits are known to those skilled in the art to effect this functionality.

A current source 240, such as a current mirror, optionally receives a source of current 242 and a control signal 244 (VCASP). Connections 246, 246' couple the current from the source 240 to column selector 230, and if present, second column selector 230'. As shown, the coupling lines 246, 246' are separate wires (designated "a" to designate a number of wires equal to a). Further, one or more sources of current 242 may be supplied. As will be described in connection with FIG. 10C, below, the value of the current may be static, or may vary over time (such as in the application of a pulsed waveform, sinusoidal waveform, square wave, sawtooth, etc.). Generally, any desired varying waveform may be utilized.

Utilizing the structure shown in FIG. 9, each of the unit cells 212 may be activated at a given time. Alternatively, certain unit cells 212 may be activated and yet other unit cells remain inactive. By way of example, if a given column has been selected at a first value, each of the unit cells within that column which are associated with one or more selected rows selected by the row selector 220 will be activated at the value corresponding to that level of the voltage on the column. Yet other unit cells within that same column may be placed at the same or a different level by coupling to the second column selector 230', where the one or more row lines associated with those unit cells are driven by the second row selector 220'. Thus, within one column of unit cells, each unit cell 212 may be either driven at a value corresponding to the signal on the column 234 associated with the column selector 230, or with the value on the column associated with the second column selector 230', or be in an undriven, unconnected, floating or high impedance state. In a like manner, other columns may be set to desired levels of output. In this way, the entire array of unit cells may be placed in the desired state or set of states. The use of the terms 'levels of output' and 'desired state' include signals which vary as a function of time. Additionally, more values within a given column 234, 234' may be added, such as through the addition of further column selectors and column lines which are coupled to selected unit cells 212.

Figures 10A, 10B:
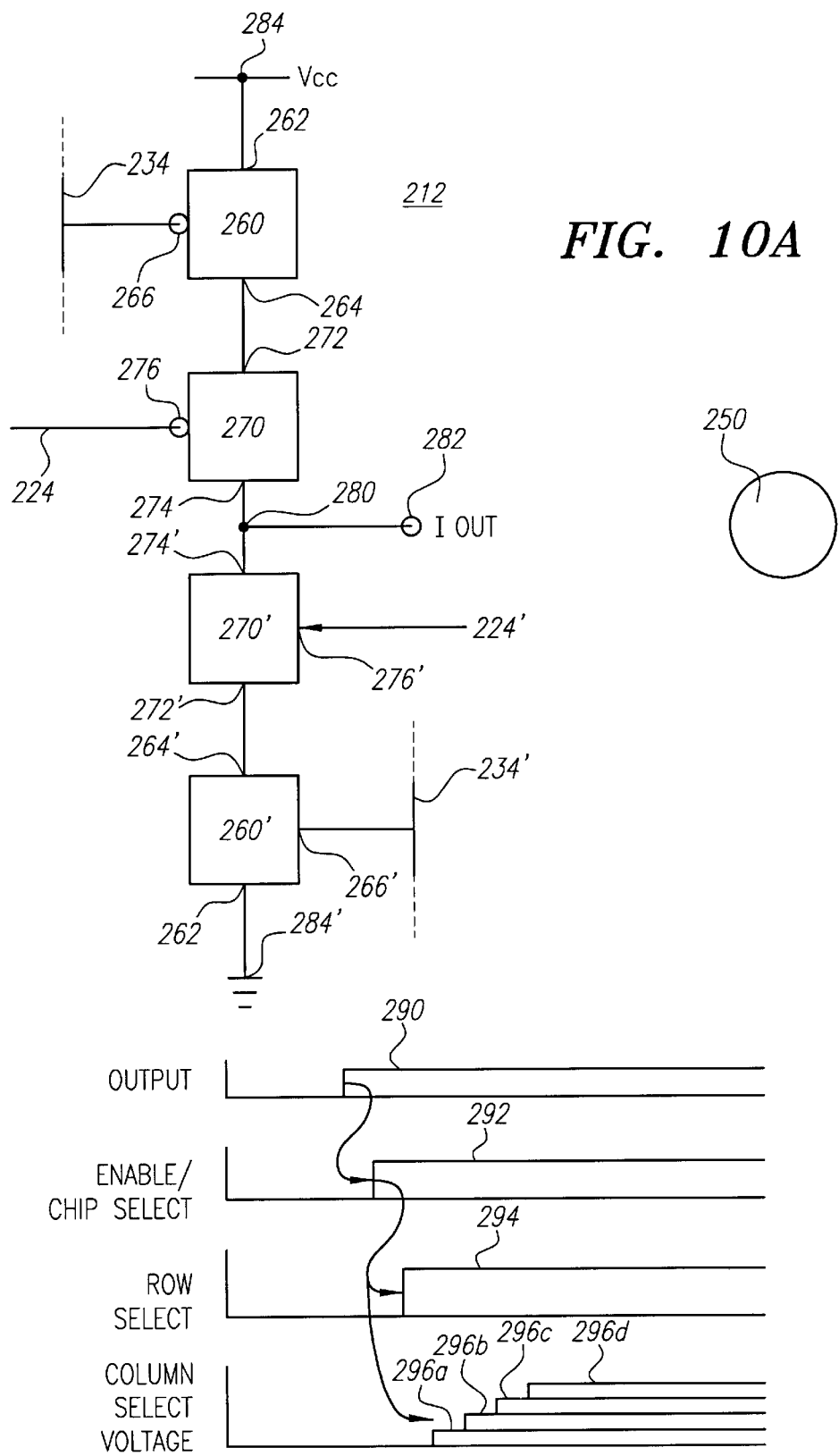
FIG. 10A is a circuit diagram of a functionalized unit cell usable with the system of FIG. 9.
FIG. 10B is a voltage/timing diagram for the circuit of FIGS. 9 and 10A.

FIG. 10A shows a schematic block diagram of a unit cell 212 and return electrode 250. To the extent possible, the numbering convention in FIG. 10 corresponds to that adopted in FIG. 9. A variable current control element 260 includes an input 262, an output 264 and a control element 266. The control element 266 is coupled to a line, such as the column line 234, which is in turn coupled to the column select 230. A selector switch 270 includes an input 272, an output 274 and a control element 276. The control element 276 is coupled to a control line, such as a row line 224. The output 264 of the variable current control element 260 is coupled to the input 272 of the select switch 270. The output 274 of the select switch 270 couples to a node 280 which provides the output current 282, $I_{out}$. A first potential 284, e.g., Vcc, is provided to input 262 of the variable current control element 260.

In operation, application of a signal on row line 224 to the input 276 of the select switch 270 provides a conductive path between node 280 and output 264 of the variable current control element 260. The signal value applied to the column line 234, which is coupled to the input 266 of the variable current control element 260 serves to provide a variable amount of current flowing through the series connected variable current control element 260 and select switch 270 between the first potential node 284 and the output node 280. A return electrode 250 serves to complete the circuit, though it will be appreciated that the return electrode 250 may be yet another unit cell 212.

In the preferred embodiment, the variable current control element 260 is a transistor, such as a field effect transistor, and most particularly a MOSFET. The select switch 270 is preferably a transistor, more preferably a field effect transistor, and most particularly a MOSFET. Various types of particular implementation may be utilized, whether C-MOS, N-MOS, CMOS, bipolar, gallium arsenide, or otherwise, so long as consistent with the functional requirements of the system. Further, in the preferred embodiment, a matching arrangement of a second variable current control element 260' and second select switch 270' couples between a second potential 284' and the output node 280. Optionally, channel lengths of the various devices may be arranged such that a symmetric arrangement is implemented. For example, in a CMOS implementation, the p-channel select device may have a shorter channel length than the n-channel device, to compensate for the differing electron/hole mobility. (e.g., 80 $\mu$v. 126$\mu$ channel length). A similar numbering s primes. The discussion regarding the circuit, above, applies to the circuitry including the second variable current control element 260' and second select switch 270'.

FIG. 10B shows signals as a function of time for exemplary control signal of the unit cell 212. The generation of the output signal 290 indicates the completion of the entry of the data into the selectors 220, 220', 230, 230'. The output signal 290 may then be used to trigger or activate the enable signal 292. The enable signal 292 in turn may permit the select signals for the row select 294 and column select signals 296A, 296B, 296C and 296D pass to the unit cell 212. As depicted, a single row select signal 294 is provided, wherein that signal is provided to a select circuit 270, 270' having preferably bistate operation. The column select signals 296A, 296B, 296C and 296D may be of differing values, preferably of more than two values, in the preferred embodiment comprising at least four values, which are then provided to the inputs 266, 266' of the variable current control elements 260, 260'. As explained further, below, these values may be static or dynamic.

Figure 10C:
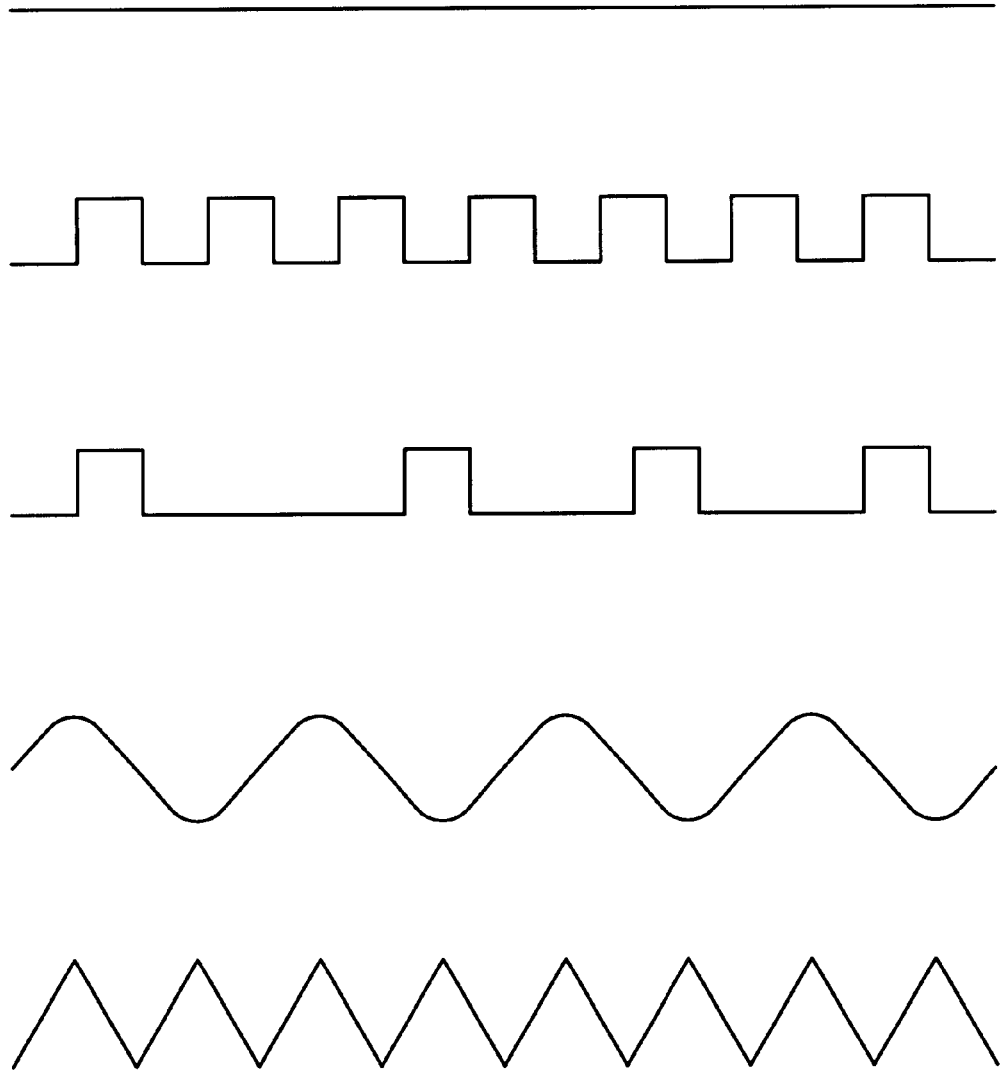
FIG. 10C are current diagrams as a function of time for the circuit of FIGS. 9 and 10A.

FIG. 10C depicts exemplary values of current (or voltage) as a function of time which may be supplied to the electrodes. In one embodiment, a static, direct current (sourced or sinked), which does not vary as a function of time may be supplied. While the value of the current is static, it will be understood that the selection, typically digital selection, of whether to permit this current to drive the electrode or not is utilized, such that the electrode is selectively driven as a function of time. The second waveform in FIG. 10C shows a square wave. The square wave may be for unit directional current or bidirectional current. An offset bias may be utilized as desired. As shown in the third waveform in FIG. 10C, the waveform may have a periodicity which has a subcomponent waveform included within it. The fourth waveform in FIG. 10C shows a generally sinusoidal waveform. The fifth waveform in FIG. 10C shows a sawtooth waveform. It will be appreciated that any waveform consistent with the goals and objects of this invention may be utilized in conjunction with the devices and methods disclosed herein. By supplying a waveform, most particularly, a current waveform, which is selectively controllable by digital selection (such as through the action of the row selector 220 in FIG. 9), a high degree of flexibility and control is achievable. Further, the waveforms supplied to various test sites within the device need not be the same. For example, the first column may have a static, direct current waveform applied to it, the second column may have a square wave waveform applied to it, whereas the third column has a sinusoidal waveform applied to the microlocations in that column as selected by the row selector, and so on.

The waveforms for the current may be generated on the chip or off chip. In practical implementation, the waveforms may be generated through the use of digital to analog converters (DACs), digital signal processors (DSPs), variable current waveform generators, on-chip memories, all optionally under control of a control system utilizing a central processing unit (CPU) or other version of microprocessor control.

Figure 11:
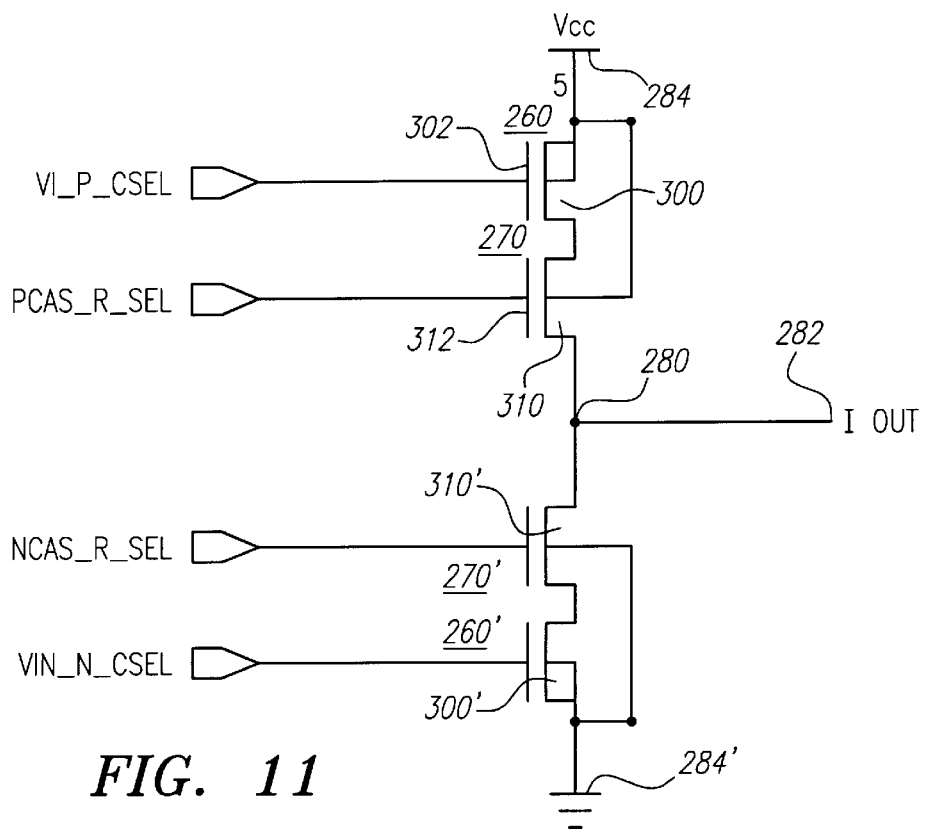
FIG. 11 is a component level circuit diagram of a unit cell usable with the system of FIG. 9.
Figure 12:
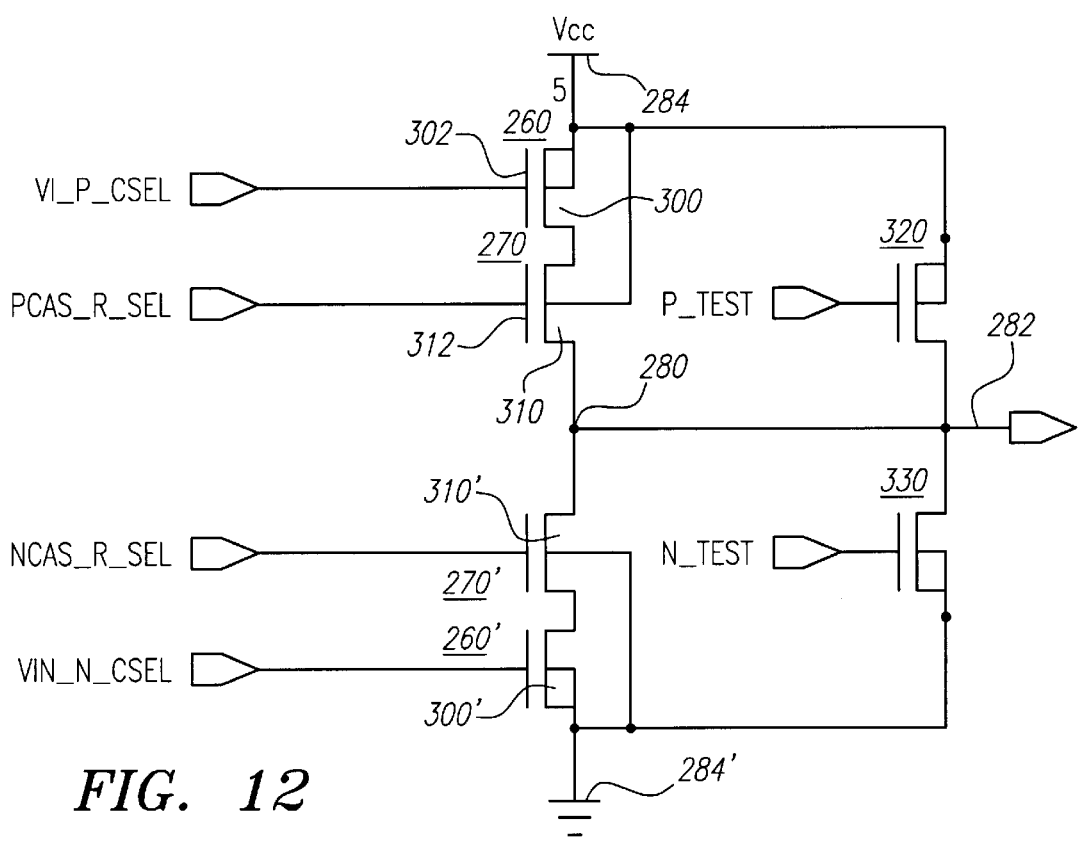
FIG. 12 is a component level circuit diagram of a unit cell including additional test circuitry usable with the system of FIG. 9.

FIGS. 11 and 12 are circuit schematics for a driving circuit for a unit cell in one embodiment of this invention. FIG. 12 expressly includes test circuitry, such as test transistors 320, 330, whereas FIG. 11 does not. The common aspects of the figures will be described together.

In one preferred embodiment of a unit cell 212, a symmetric arrangement is utilized. A first column select unit 260, preferably a transistor, and a first row select unit 270, also preferably a transistor, are in series relation between a first source 284, e.g., voltage and/or current source, and a node 280, typically a current output node. In the preferred embodiment, the column select transistor 300 may be precisely controlled under application of a gate voltage such as from the column shift register memory (See FIG. 15). Preferably, the select units 260, 260' may differ from each other in their controllability, such as by varying the channel length in the control transistor. Thus, by application of potentials from the row selector 220, 220' and column selector 230, 230', application of potential to the control gates 302, 312 results in output of current 282 at the unit cell.

The unit cell circuit 212 may further include a second column select unit 270', preferably a transistor 300', and a second row select unit 270', also preferably a transistor 310', used in series relation between a second source 284', e.g., voltage and/or current source, and a node, typically the previously referred to node 280, i.e., a current output node. In the preferred embodiment, the first source 284 is a supply potential Vcc and the second source 284' is a reference potential, such as ground. Preferably the nodes are the same node 280, such that there is a series connection between Vcc 284 and ground 284' of the first column select unit 260, 260' and first row select unit 270, the node 280, and the second row select unit 270' and the second column select unit 260'.

In yet another form of operation of the circuit, or alternatively, a different mode of operation of the circuit shown in FIG. 11, the circuit may be tested for continuity by simultaneously activating each of the first and second row and column select transistors 260, 270, 260' and 270. In this way the source 284 and sink 284' are directly conductively connected.

In yet another aspect of the preferred embodiment, test circuitry is included. FIG. 12 shows a schematic diagram of such a system. A first test transistor 320 spans the first column select transistor 260 and first row select 270 transistor. Likewise, a second test transistor 330 spans the second column select transistor 260' and second row select transistor 270'. Selective activation ensures continuity of the circuit.

While the circuitry described herein may be implemented in any known technology consistent with the achievement of the desired functionality of this system, one preferred mode of implementation is through CMOS circuitry. In one implementation of the circuits of FIGS. 11 and 12, the column select devices 260, 260' include a relatively long channel length. These relatively large field effect transistors serve to provide more accurate current control. By way of example, one implementation of this circuitry is in transistors having a 6 micron channel width. The upper column select unit 260 (controlled by VI_P_CSEL) has a channel length of 80 microns, and the lower column select unit 260' (controlled by signal VIN_N_CSEL) has a channel length of 126 microns. The difference in channel lengths reflects the difference in mobility of electrons and holes, and seeks to balance these two devices. By way of comparison, the remaining devices in FIGS. 11 and 12 have a 6 micron channel width, and a 4 micron channel length. Alternative implementations of the unit cell 212 include series connection of transistors, including dedicated series selection transistors for a row select and column select, plus an additional transistor for output level (current or voltage) select. More broadly, any circuit which receives cite selection information (e.g., row and column select) and value and/or polarity information and causes the outputting of the desired current or potential may be utilized.

Figure 13:
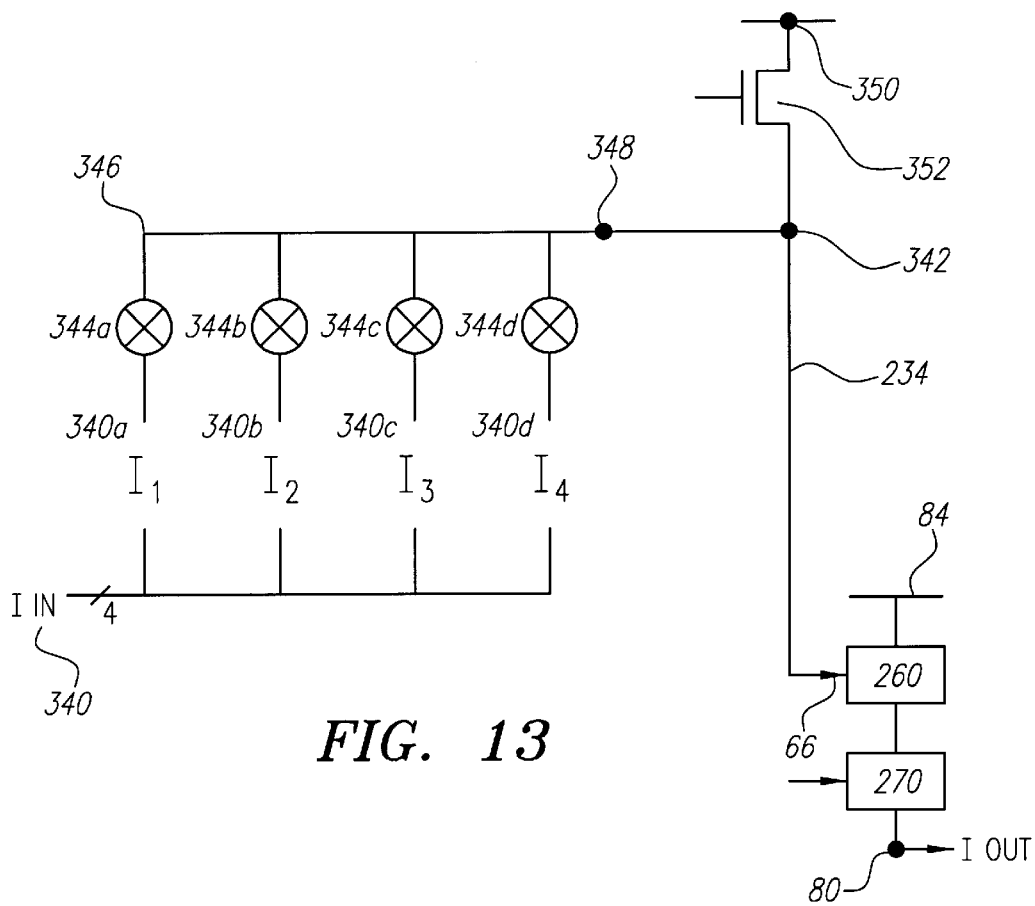
FIG. 13 is a schematic diagram of a circuit for providing current control in an active electronic device.

FIG. 13 shows a schematic view of a current control system useful in the inventions disclosed herein. To the extent possible, the numbering convention is consistent with those of other drawings. The circuit serves to receive an input current 340 which is selectively controllable so as to generate a voltage at node 342 which is in turn coupled to a line 234 (shown to be the column line 234) which in turn is coupled to the control element 266 of the variable current control element 260. The variable current control element 260, row select switch 270, first supply voltage 284 and output current from node 280 are as described previously. Similarly, a current controlled circuit may be utilized to control a symmetric circuit (e.g., elements 260' and 270' of FIG. 10).

The input currents 340 are provided to control elements 344. Each current of a given subscript is provided to a control element 344 of like subscript. The control element 344 serves to selectively provide current at the output 346. As shown, the current outputs 346 are summed such that the current at node 348 may be varied based upon the states of the switches or control elements 344a–d. A voltage divider arrangement is then provided wherein a potential 350 is provided to resistor 352 which connects to node 342. By supplying the current at node 348 to node 342 and then through resistor 352, a variable voltage is provided at node 342. Optionally, the resistor 342 may be a device which, such as a transistor, which is conductive only in the event that current will be supplied to node 348. Thus, in the event that each switch 344a–d is to remain off, such a circuit would also not include the resistor 352 in any state of conduction in that event. (See FIG. 15 for a detailed implementation).

Figure 14:
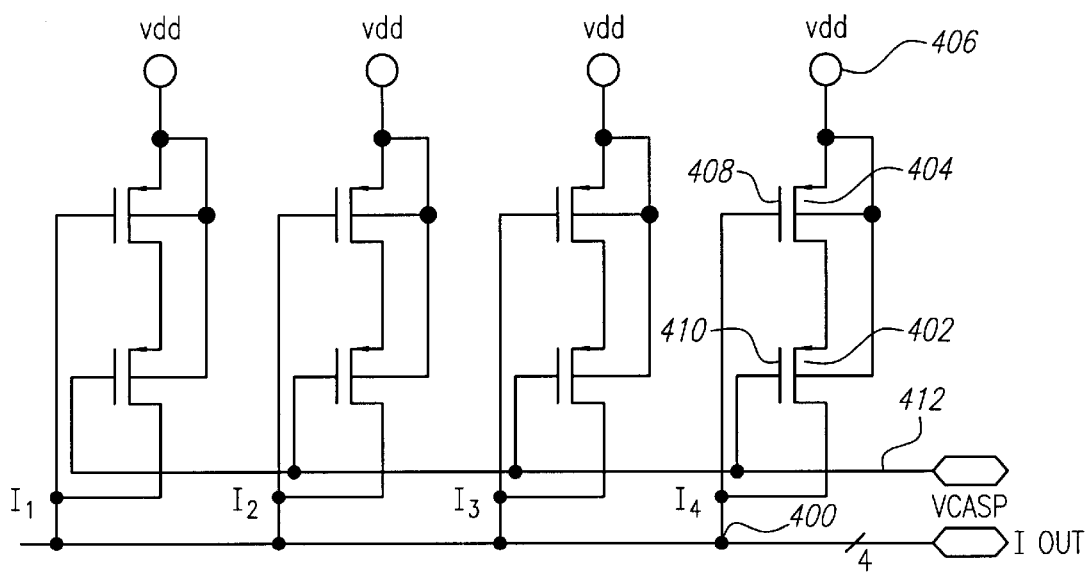
FIG. 14 is a component level circuit diagram of current mirrors.

FIG. 14 shows a detailed circuit diagram for a portion of the current mirror for use in the system. Four identical circuits are shown in FIG. 14, and the description with respect to one circuit will apply to all circuits equally. A current node 400 couples to the output of a first transistor 402 and second series connected transistor 404 which is in turn connected to a first potential 406 (Vdd). Optionally, the transistors 402, 404 are biased to or connected to the supply voltage 406. The control gate 408 for the second series connected transistor 404 is connected to the current node 400. The current node 400 is also connected to the output (source or drain) of first transistor 402. The control gate 410 of the first control transistor 402 is controlled by a signal 412. The signal 412 serves as a select signal for the current mirror. The select signal 412 is supplied to the current mirrors to cause selective provision of the current from current nodes 400 to the column select circuitry.

Figure 15:
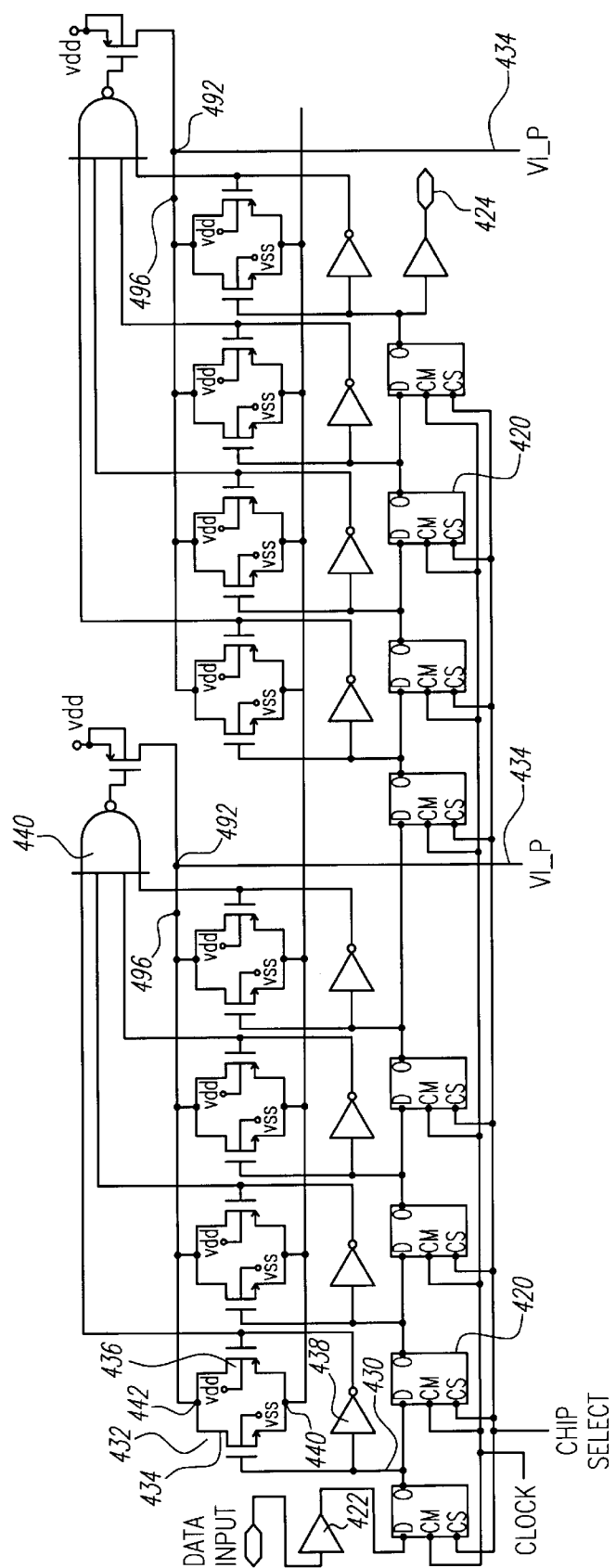
FIG. 15 is a component level circuit diagram of column selection circuitry.

FIG. 15 is a detailed circuit diagram of a column select circuit (See, e.g., column selector 230 in FIG. 9). A shift register arrangement is provided by a series of flip-flops 420, the first of which receives as an input the input information (Q(0)), optionally inverted by inverter 422. As explained in connection with FIG. 9, an optional output 229 may be provided from the selector, e.g., shift register 230. As shown, two stages, each comprising four bits, is shown for a shift register. In implementation, a 20×20 matrix or array of unit cells would require 80 bits in the shift register 126 if 4 bits are assigned to each column. The outputs 430 are provided as control signals to current control circuitry 432. As shown, the current control circuitry consists of a parallel arrangement of a first transistor 434 and second transistor 436, of opposite conductivity type, having their control gates coupled to the signal 430 as supplied directly to the first transistor 434 and through an inverter 438 to the second transistor 436. In operation, the current supplied to node 440 is then selectively passed to output node 442 under control of the signal 430. The current at the output node 442 is summed with the output currents from the three other control circuits 434 for the column position, the summing occurring by or before node 496.

The summed current at node 496 is passed to node 492 which may serve as a voltage tap for column line 434. Logic 440, here shown to be a NAND gate, receives as inputs the outputs of the inverters 438. The outputs of the inverters 438 are provided to the NAND gate 440, which logically serves as an OR for the various inputs. Thus, the selection of any of the various current sources serves to activate the gated transistor controlled by the logic element 440.

The shift register 126 includes multiple series connected flip-flops 420. The value signal is provided as input to the inverter 422 and then to the D input of the flip-flop 420. A clock signal (CM) and chip select signal (CS) are provided. The output of the last flip-flop 420 (right most in FIG. 15) is provided to an inverter which provides the output bit at node 424.

Figure 16:
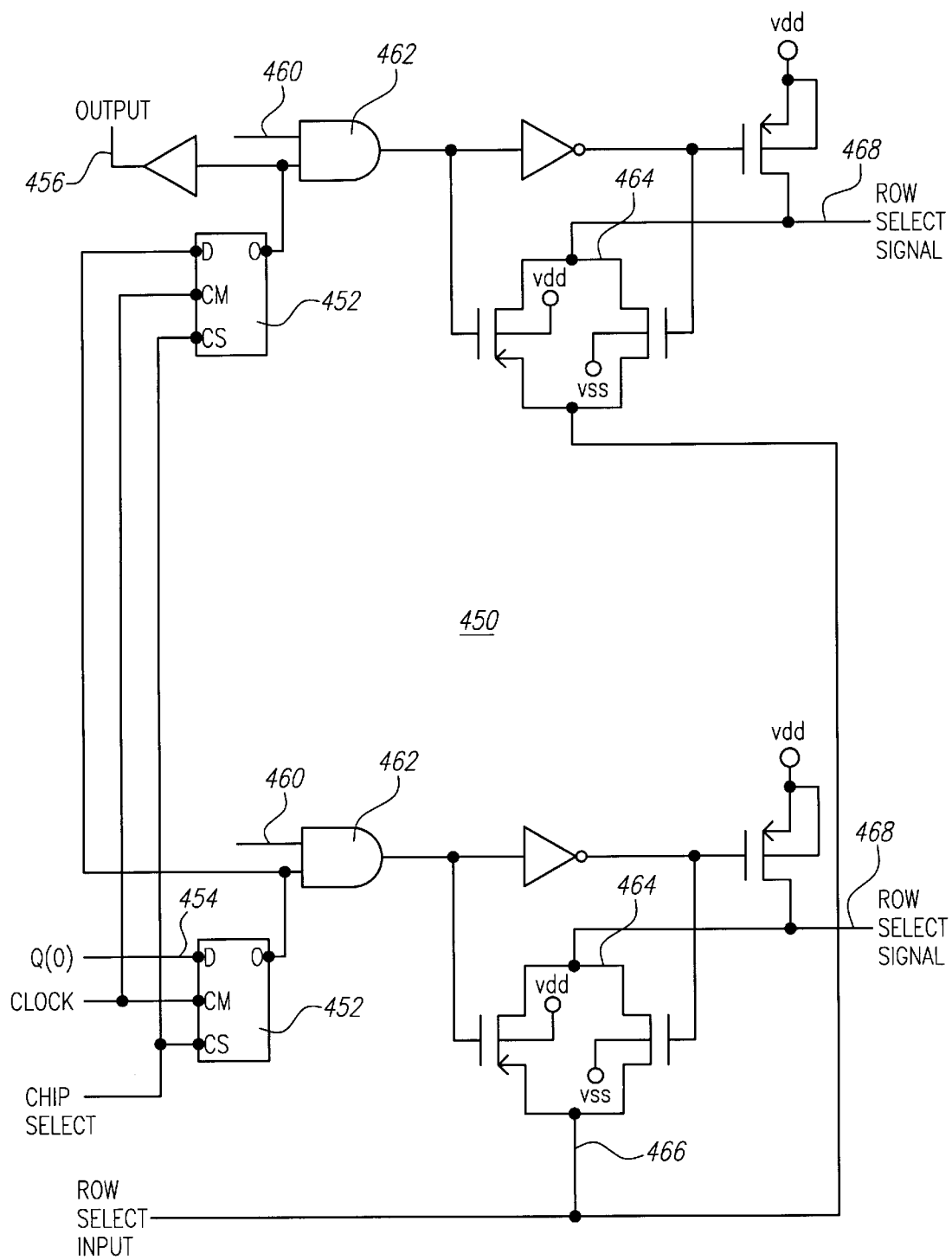
FIG. 16 is a component level schematic diagram for a row select circuit.

FIG. 16 shows a component level schematic for a shift register 450. Flip-flops 452 receive an input 454 (Q(0)) which is passed to other flip-flops 452 via the Q output of one flip-flop to the D input of the next flip-flop 452. Optionally, an output 456 provides an indication of the most significant bit (or other indicator of loading) from the shift register. The enable signal 460 is provided as input to logic 462 (shown here to be a NAND gate) which also receives as input the output (Q pin) of the associated flip-flop 452. The output of logic 462 controls pass circuitry 464 which serves to selectively pass the signal 466 which if passed through circuitry 464 constitutes the row select signal 468. The circuitry repeats for the number of stages in the shift register 450, and the description provided here applies to those stages.

Figure 17:
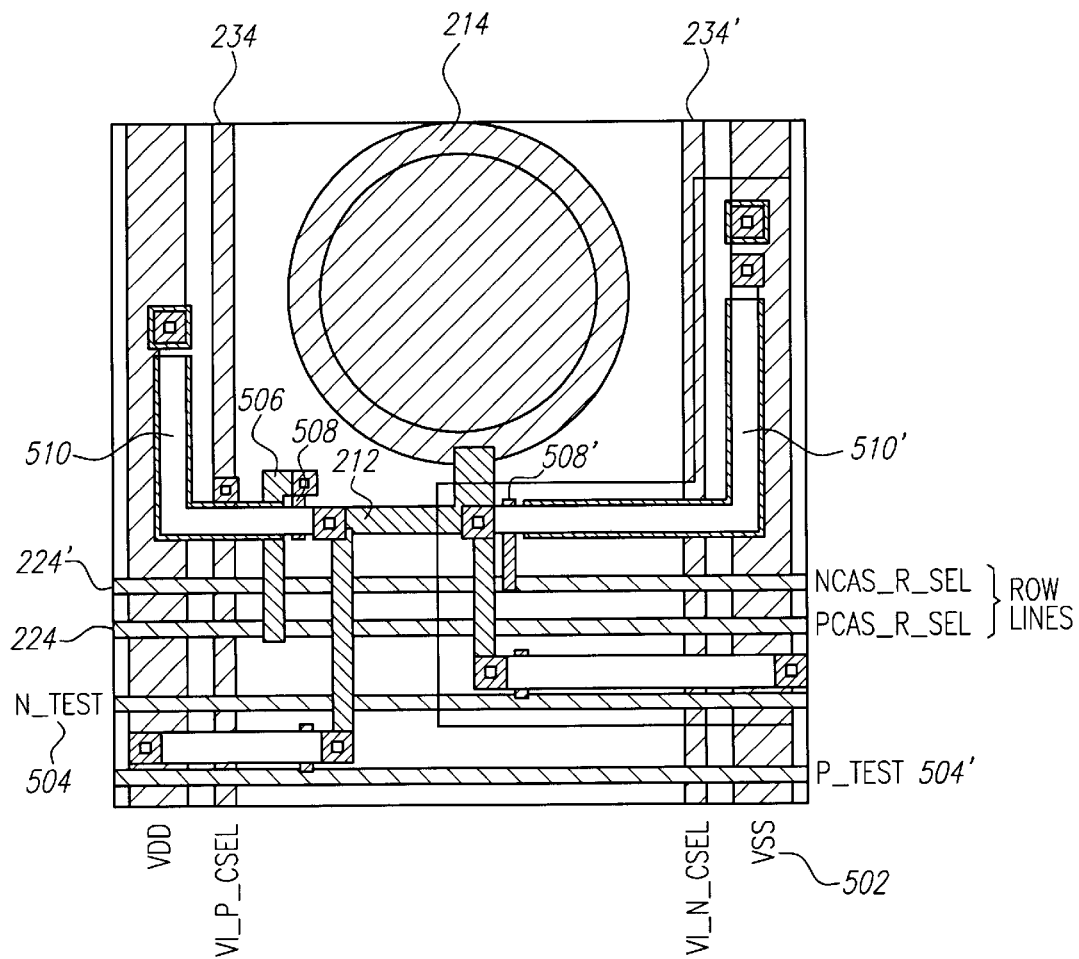
FIG. 17 is a plan view of a physical layout of a unit cell.

FIG. 17 shows the layout for one implementation of a unit cell. Column lines 234, 234' are shown running vertically, which couple to the column selectors (See FIG. 9). Row lines 224, 224' are shown running horizontally. The supply voltage VDD 500 and the second voltage 202 (VSS e.g., ground) are disposed running generally parallel to the column lines, 234, 234'. The optional test control lines 504, 504' provide control signals for the n test and p test circuitry, respectively. Row line 224 is connected by conductive member 506 to gate 508 which overlies the channel region underneath. Likewise, the row line 224' couples to gate 508' which overlies the channel region for the select transistor. The column lines 234, 234' are electrically coupled to gates 510, 510' which overlie the channel region which are then coupled to the first supply voltage VDD 500 and second supply voltage VSS 502, respectively. The channel length underlying the gates 510, 510' differ, the difference in length being selected such that the operative devices have similar suitable properties. The output of the switching transistors controlled by gates 508, 508' are provided through conductive member 512 to electrode 514.

Figure 18:
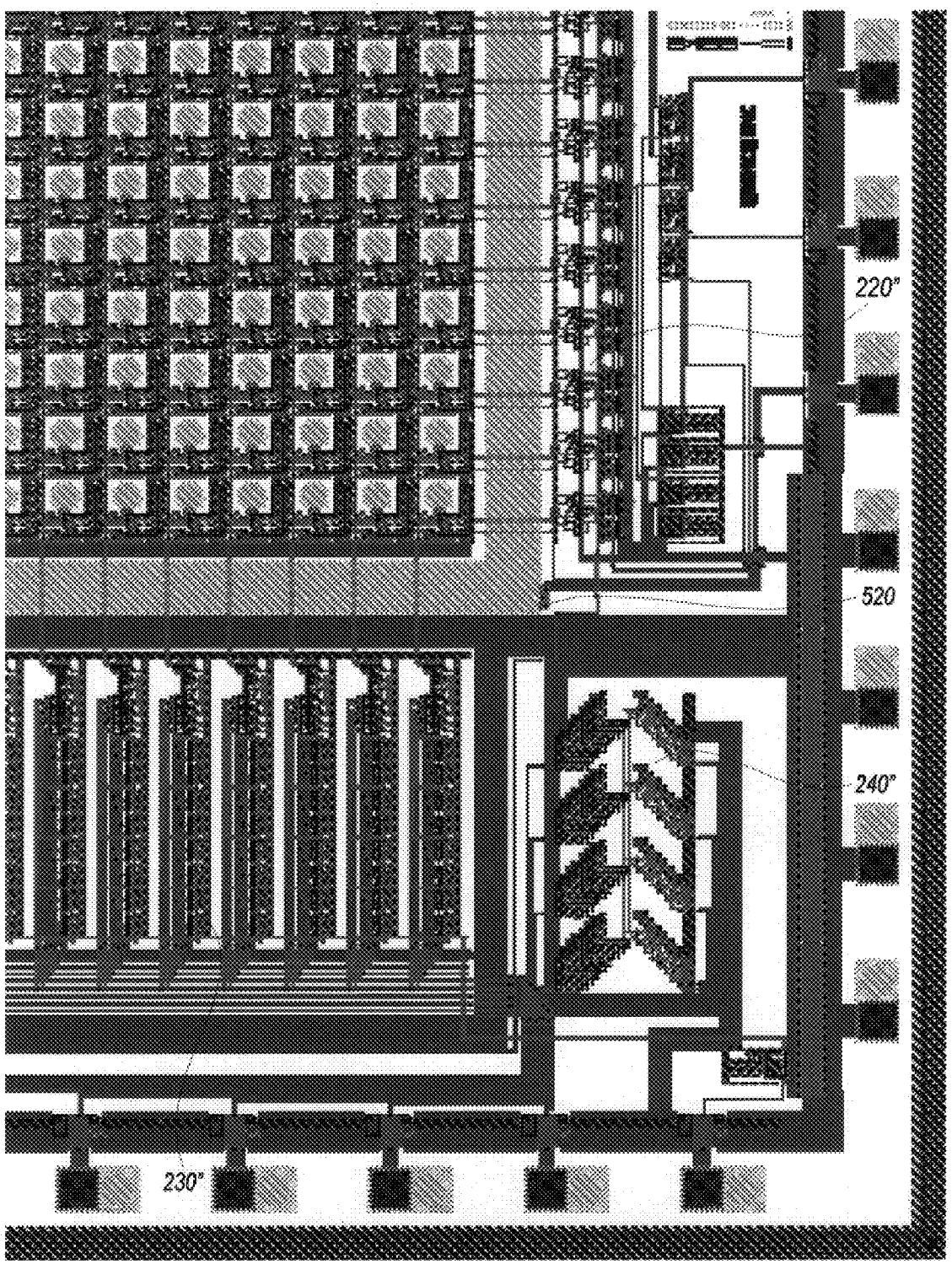
FIG. 18 is a plan view of a layout of a portion of the 20×20 test site unit.

FIG. 18 shows a plan view of a portion of a 20×20 array of unit cells. FIG. 18 shows a portion of the overall chip, recognizing that the structures such as the unit cells, shift registers, row and column decoders and current mirrors are typically repeated identically throughout the chip. A plurality of unit cells (shown in detail in FIG. 17) are included. Counter or return electrodes 520 are preferably disposed at the periphery of the array of the unit cells. The electrodes 520 preferably encompass or circumscribe the unit cell array. Optionally, multiple electrodes may be utilized to encompass the array. In the preferred embodiment, 4 L-shaped electrodes bracket the array (a corner of one being shown), each electrode bracketing substantially ¼ of the array. These electrodes may be utilized to move undesired materials, and to serve as a dump or disposition electrode. Row selectors 220" (so labeled to correspond to the numbering in FIG. 9) are disposed to the right of the array and electrode 520 in FIG. 18). Column selectors 230" are disposed exterior to the array and the electrode 520. Current mirror circuitry 240" is optionally disposed at the corners of the chip. The selection and arrangement of components on chip is made to optimize the functionality of the device. Inclusion of components on chip, which is typically the disposable component, permits local control of finctionality, though with increased device costs. While various arrangements are possible, the structure shown in FIG. 18 is the preferred embodiment for the 20×20 chip.

Figure 19:
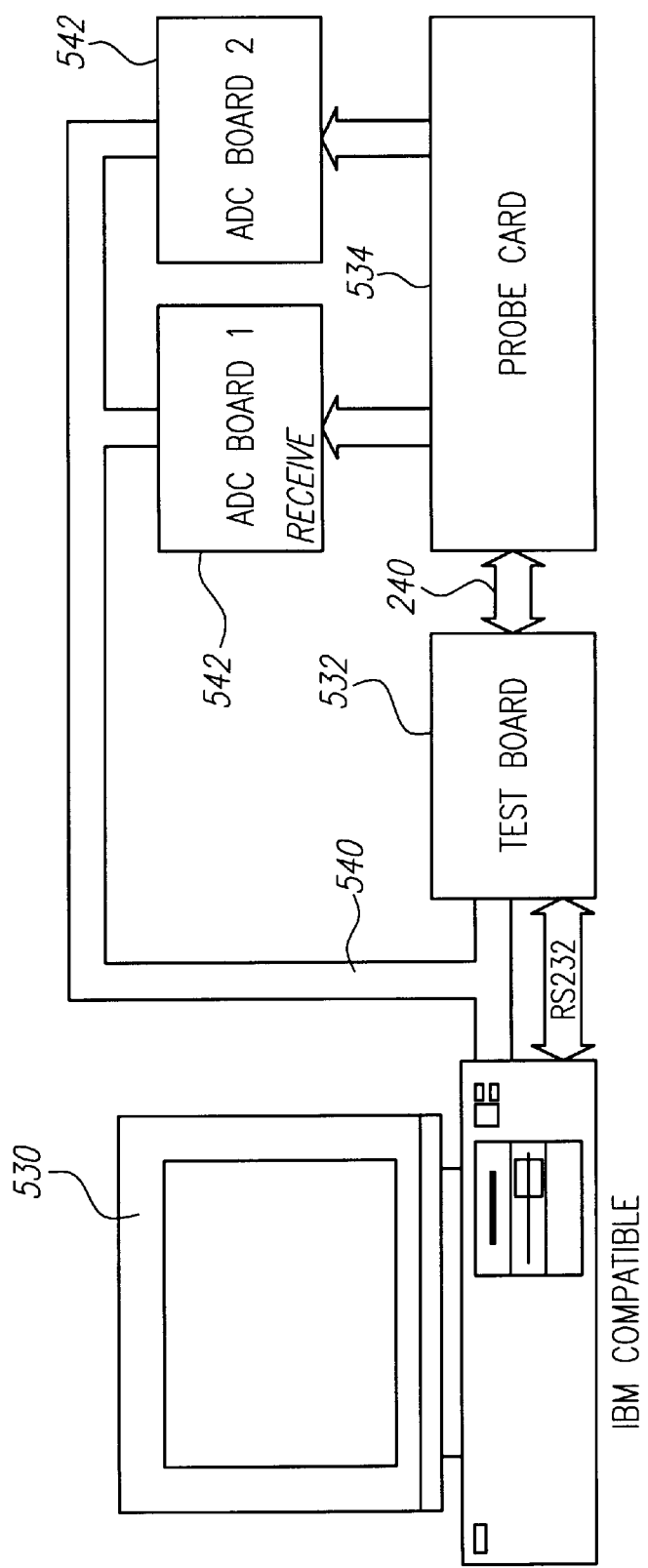
FIG. 19 is a block diagrammatic view of the overall control and test system in one aspect of this invention.

FIG. 19 is a schematic diagram of the overall system. A control computer 530 is coupled to a test board 532 and probe card 534 via buses 540. Optionally, a connector, such as an RS232 connector is utilized. The probe card 534 interfaces with the actual active electronic device. The output from the device may be provided to receiving systems 542, which may include analog to digital converters for provision of digital data via the bus 540 to the computer system 530.

Figure 20:
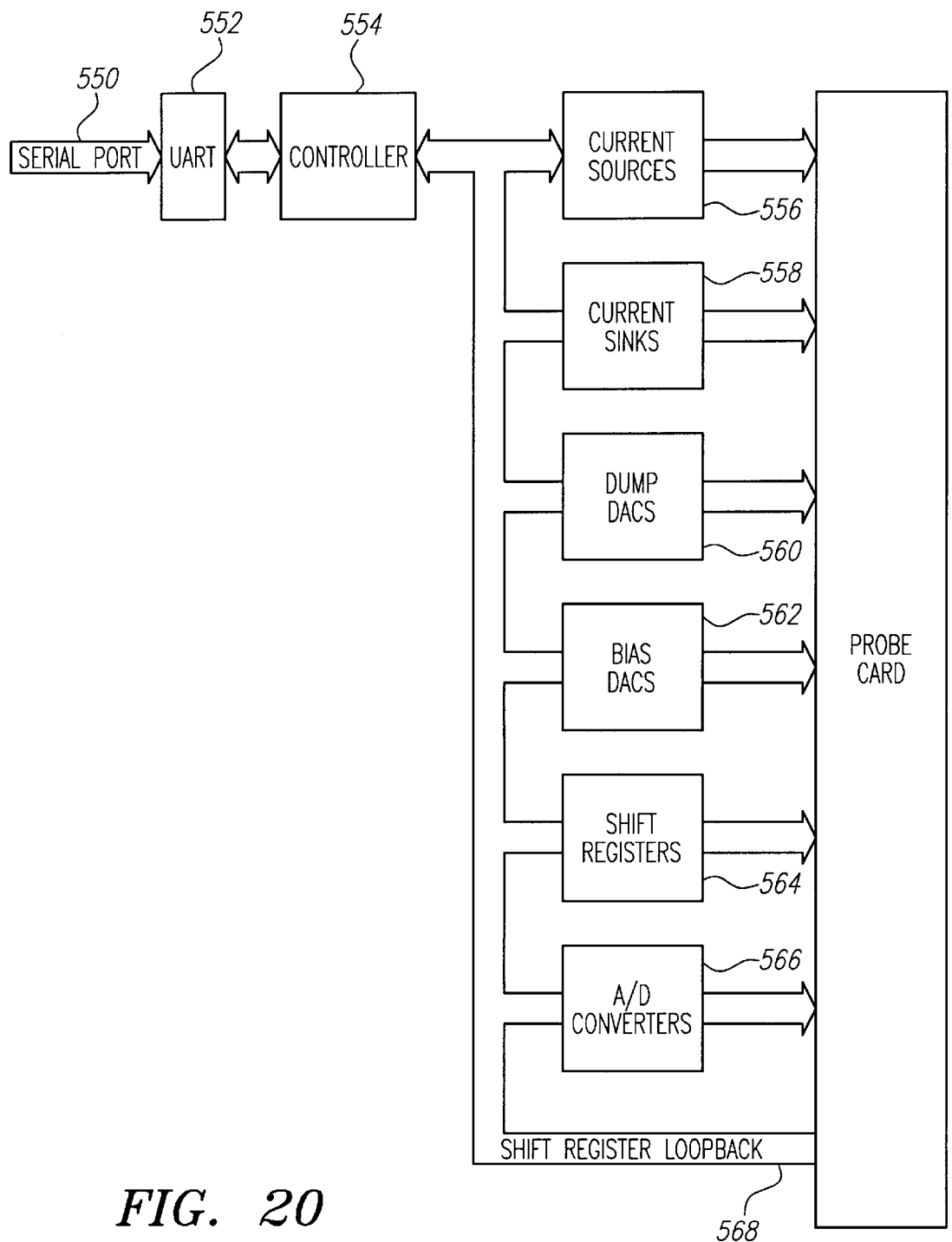
FIG. 20 is a schematic block diagram view of the interconnection between an input system and a probe card for connection to an active biological matrix system.

FIG. 20 is a expanded block diagram of the test board and probe card of FIG. 19. The serial port connection 550 couples to a universal asynchronous receiver transmitter (UART) 552 onto a controller 554. Bus interconnection then couples to current sources 556 and current sinks 558. Various digital to analog converters such as the dump DACs (digital-to-analog converters) 560 and bias DAC 562 are provided. Shift registers 264 coupled to the probe card 534. Analog to digital converters 556 may receive an output signal, such as from the probe card 534. If the shift registers include an output (See output 229, 229', 239, 239' and FIG. 9) a shift register loopback 568 may be provided.

Figure 21:
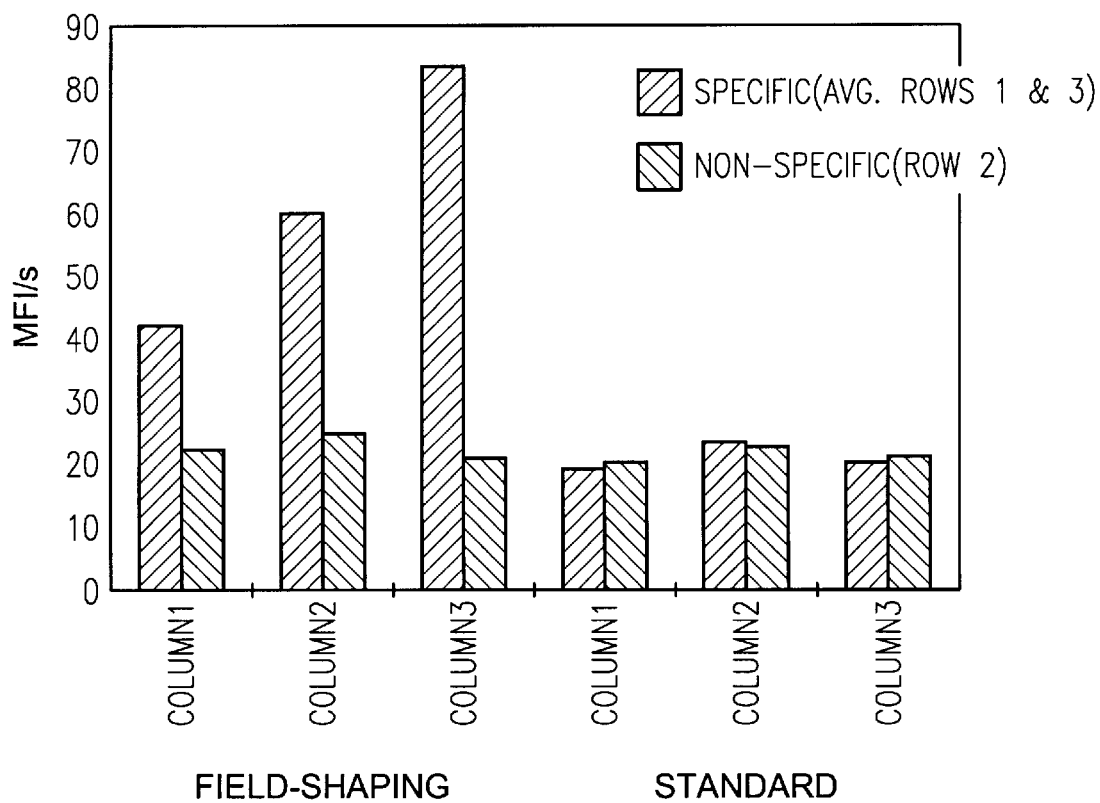
FIG. 21 is a graph of hybridization as a function of specific and non-specific hybridization for field-shaping and for no use of field shaping.

FIG. 21 shows a graph of electronic hybridization utilizing the chip of FIG. 2. The graph shows the fluorescent intensity, in MFI/s as a function of column number. The three bar graphs labeled column 1, column 2 and column 3 utilize field shaping, and show specific hybridization on the left bar graph in comparison to non-specific hybridization on the adjacent right hand column. The three couplets of bar graphs labeled column 1, column 2 and column 3 above the designator "standard" show the same system but without field shaping. The discrimination between specific versus non-specific binding is significantly less than in the case where field shaping is utilized. The sequences were ATA5/ATA7/biotin, and 10 pM RCA5/BTR.

Figure 22:
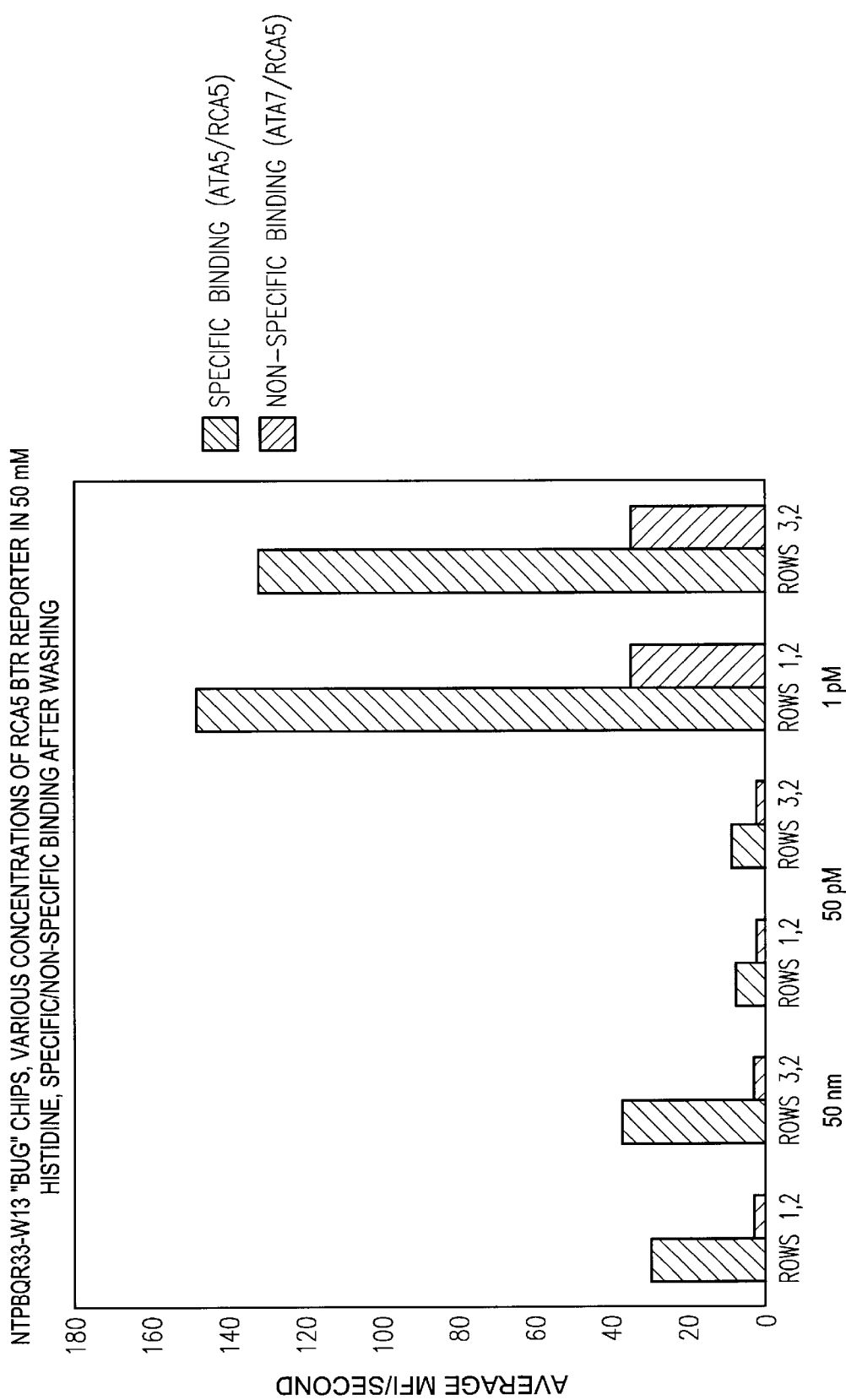
FIG. 22 is a graph of Average MFI/s at various concentrations for the embodiment of FIG. 2, at various concentrations RCA5 BTR Reporter in 50 mM histidine, showing Specific/Non-Specific Binding After Washing.

FIG. 22 shows a graph of experiments performed with the system as shown in FIG. 2. The y-axis shows the average MFI/second, and the x-axis shows various rows of various concentrations. The first couplet of paragraphs shows a 50 nM concentration of RCA5 BTR reporter in 50 mM histidine, and depicting the specific/non-specific binding after washing. The first couplet shows rows 1 and 2 comparing the specific binding (ATA5/RCA5) to the non-specific binding (ATA7/RCA5), showing a 12:1 and 50:1 improvement. The middle couplets of bar graphs show a 50 pM concentration of RCA5 BTR reporter and shows a 3.9:1 and 4.9:1 ratio of specific binding to non-specific binding signal intensity. The last set of couplet bar graphs shows a 1 pM concentration of RCA5 BTR reporter and shows a 4.4:1 and 4.0:1 ratio of specific binding to non-specific binding.

Figure 23:
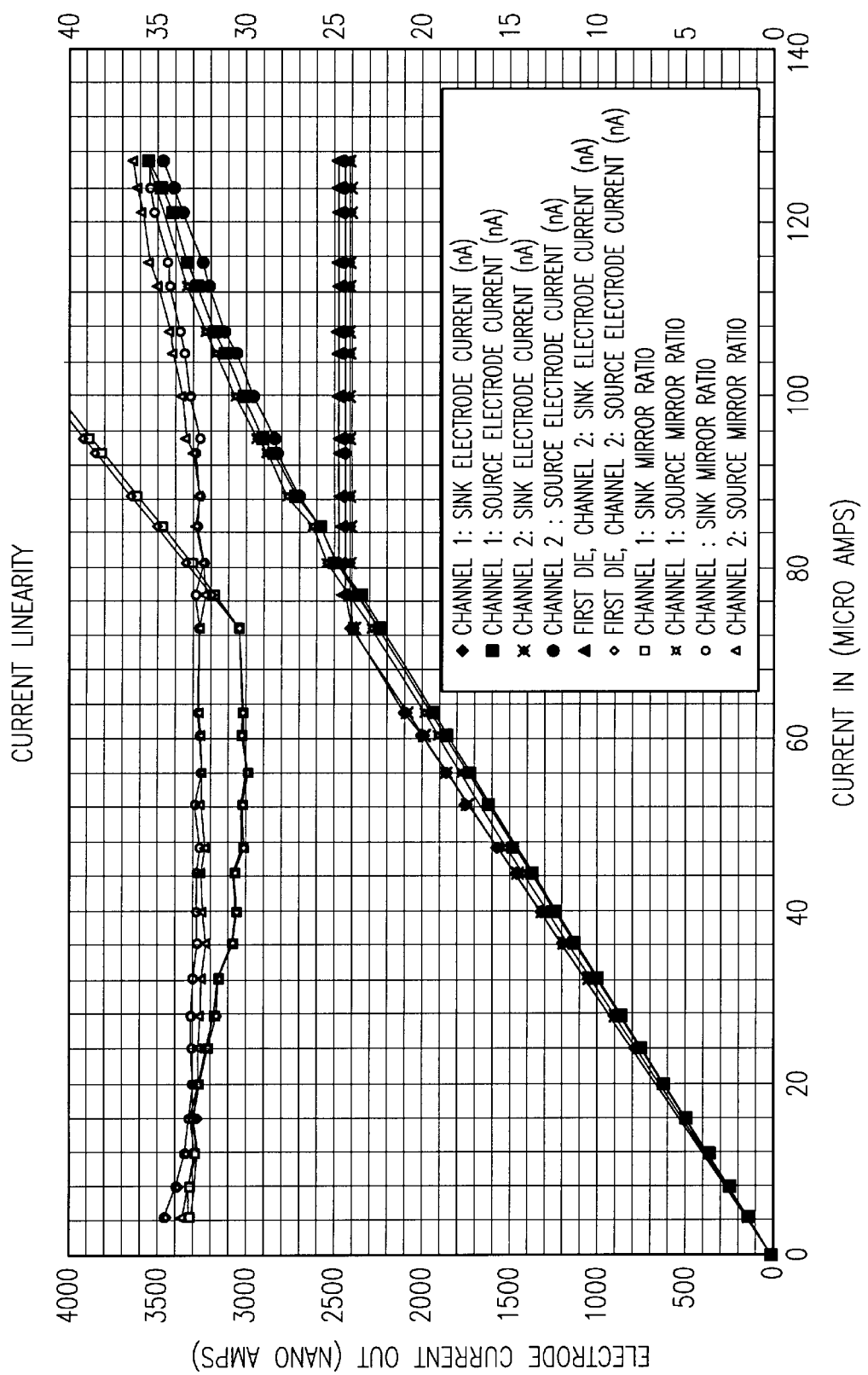
FIG. 23 is a graph of current linearity showing the electrode current output in nanoamps as a function of current n in microamps.
Figure 6B:
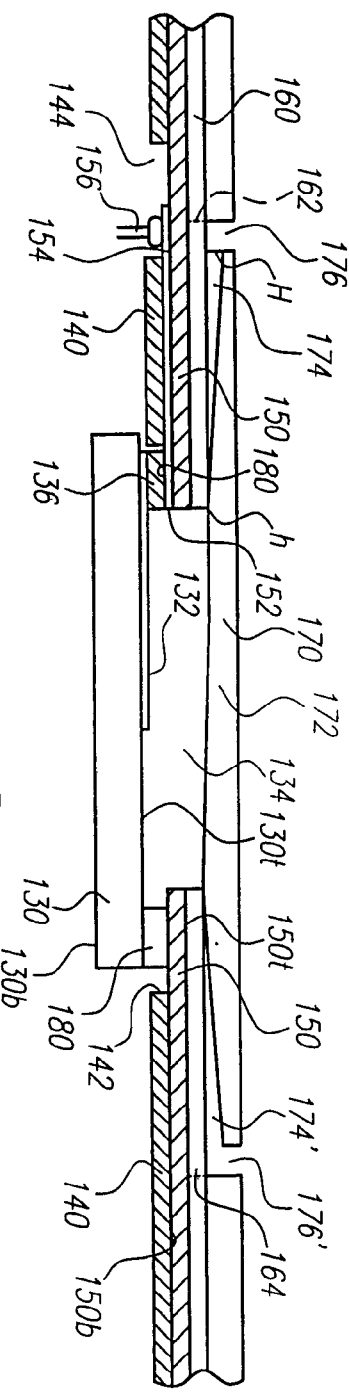

FIG. 23 is a graph of current linearity showing the electrode current output in nanoamps as a function of current input in microamps. A legend is provided to indicate the various lines on the graph.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirt or scope of the appended claims.

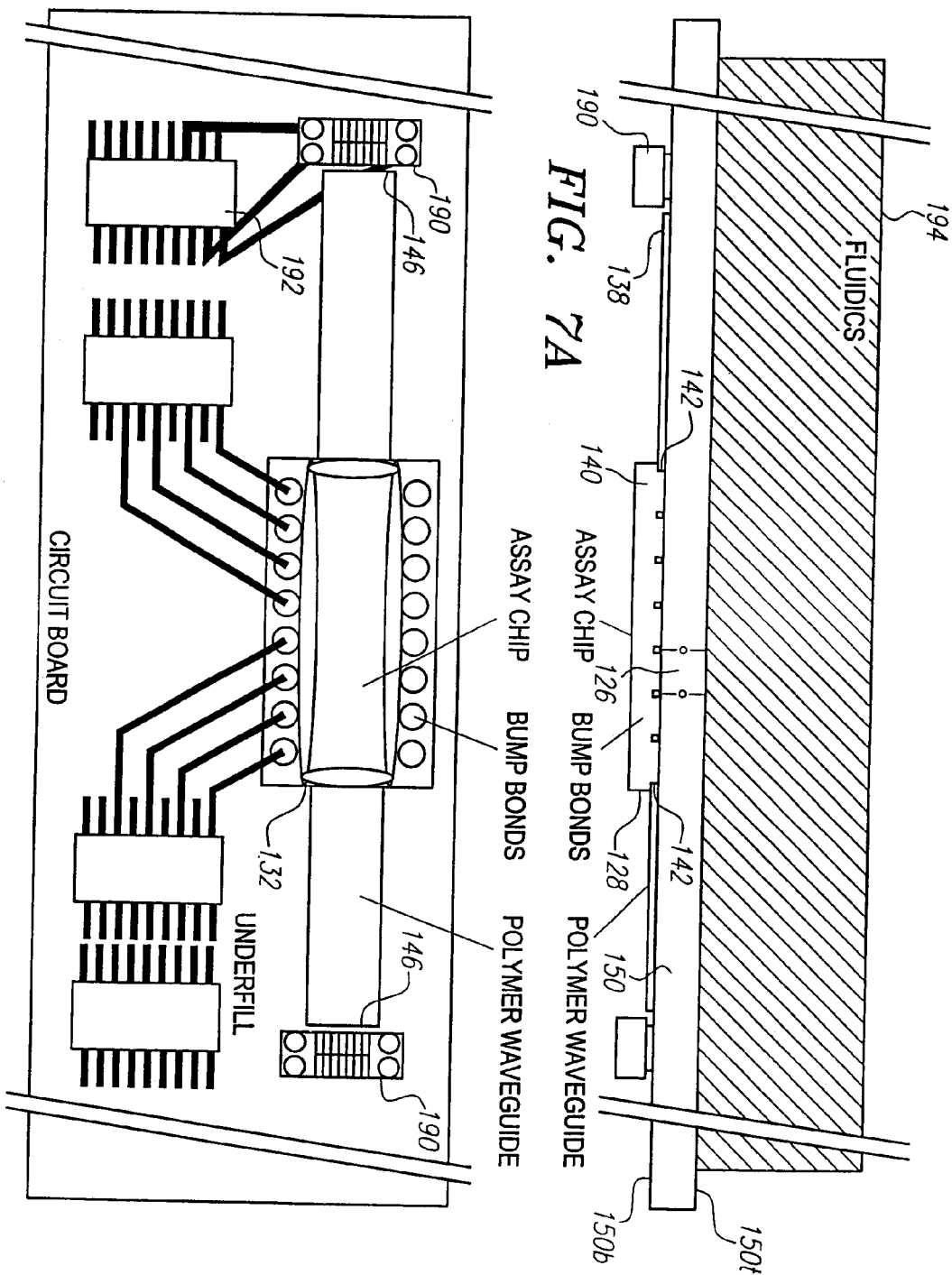

We claim:

1. A method for manufacturing a flip-chip device for performing active biological operations, the device including a substrate having first and second surfaces, the substrate including a via between the first and second surfaces, the substrate further including electrically conductive traces on at least one of the first and second surfaces, the device further including a chip having first and second surfaces, the chip including electrically conductive traces on the first surface connecting to an array of microlocations, the array of microlocations adapted to receive a fluid placed upon the substrate and through the via, the array of microelectrodes being disposed within a sealant free reaion on the first surface of the chip, the method comprising the steps of:

placing the chip adjacent to the substrate;

forming electrically conductive interconnects, interconnecting the electrically conductive traces on the first surface of the chip with the electrically conductive traces on either the first or second surfaces of the substrate;

exposing light onto the substrate and through the via, down to the first surface of the chip; and applying a light curable, wickable sealant to the interface between the substrate and the chip, said interface between the substrate and the chip lying outside the sealant free region, wherein the light at least partially cures the sealant, whereby the sealant is precluded from flowing to the sealant free region so as to leave the array of microlocations free of sealant.

2. A method according to claim 1, wherein the electrically conductive interconnects are bumps.

3. A method according to claim 1 further including the step of completing the cure of the sealant.

4. A method according to claim 1, wherein the light exposed to the substrate is UV light.

5. A method according to claim 3, wherein the step of completing the cure of the sealant is done by heat treatment.

6. A method according to claim 1, wherein the sealant is applied to the interface between the chip and substrate by wicking.

7. A method according to claim 1 further including the step of placing a flow cell on either the first or second surfaces of the substrate, the flow cell residing on a surface of the substrate opposite to the surface of the substrate adjacent to the chip.

8. A method for manufacturing a flip-chip device for performing active biological operations, the device including a substrate having first and second surfaces, the substrate including a via between the first and second surfaces, the substrate further including electrically conductive traces on at least one of the first and second surfaces, the device further including a chip having first and second surfaces, the chip including electrically conductive traces on the first surface connecting to an array of microlocations, the array of microlocations adapted to receive a fluid placed upon the substrate and through the via, the array of microelectrodes being disposed within a sealant free region on the first surface of the chip, the method comprising the steps of:

placing the chip adjacent to the substrate;

forming electrically conductive interconnects, interconnecting the electrically conductive traces on the first surface of the chip with the electrically conductive traces on either the first or second surfaces of the substrate;

applying a curable, wickable sealant to the interface between the substrate and the chip, said interface between the substrate and the chip lying outside the sealant free region, said applied sealant being of a sufficient viscosity and amount such that said sealant is precluded from flowing to the sealant free region so as to leave the array of microlocations free of sealant; and completing the cure of said sealant.

9. A method according to claim 8, wherein the electrically conductive interconnects are bumps.

10. A method according to claim 8, wherein the step of completing the cure of the sealant is done by heat treatment.

11. A method according to claim 8, wherein the sealant is applied to the interface between the chip and substrate by wicking.

12. A method according to claim 8 further including the step of placing a flow cell on either the first or second surfaces of the substrate, the flow cell residing on a surface of the substrate opposite to the surface of the substrate adjacent to the chip.

13. A method for manufacturing a flip-chip device for performing active biological operations, the device including a substrate having first and second surfaces, the substrate including a via between the first and second surfaces, the substrate further including electrically conductive traces on at least one of the first and second surfaces, the device further including a chip having first and second surfaces, the chip including electrically conductive traces on the first surface connecting to an array of microlocations, the array of microlocations adapted to receive a fluid placed upon the substrate and through the via, the array of microelectrodes being disposed within a sealant free region on the first surface of the chip, the method comprising the steps of:

placing the chip adjacent to the substrate;

forming electrically conductive interconnects, interconnecting the electrically conductive traces on the first surface of the chip with the electrically conductive traces on either the first or second surfaces of the substrate;

affixing an illumination member to the substrate such that the illumination member is disposed adjacent to and substantially coplanar with the first surface of the chip;

exposing light onto the substrate and through the via, down to the first surface of the chip; and applying a light curable, wickable sealant to the interface between the substrate and the chip, said interface between the substrate and the chip lying outside the sealant free region, wherein the light at least partially cures the sealant, whereby the sealant is precluded from flowing to the sealant free region so as to leave the array of microlocations free of sealant.

14. A method according to claim 13, wherein the electrically conductive interconnects are bumps.

15. A method according to claim 13 further including the step of completing the cure of the sealant.

16. A method according to claim 13, wherein the light exposed to the substrate is UV light.

17. A method according to claim 15, wherein the step of completing the cure of the sealant is done by heat treatment.

18. A method according to claim 13, wherein the sealant is applied to the interface between the chip and substrate by wicking.

19. A method for manufacturing a flip-chip device for performing active biological operations, the device including a substrate having first and second surfaces, the substrate including a via between the first and second surfaces, the substrate further including electrically conductive traces on at least one of the first and second surfaces, the device further including a chip having first and second surfaces, the chip including electrically conductive traces on the first surface connecting to an array of microlocations, the array of microlocations adapted to receive a fluid placed upon the substrate and through the via, the array of microlocations being disposed within a sealant free region on the first surface of the chip, the method comprising the steps of:

placing the chip adjacent to the substrate;

forming electrically conductive interconnects, interconnecting the electrically conductive traces on the first surface of the chip with the electrically conductive traces on either the first or second surfaces of the substrate;

affixing an illumination member to the substrate such that the illumination member is disposed adjacent to and substantially coplanar with the first surface of the chip;

applying a curable, wickable sealant to the interface between the substrate and the chip, the interface between the substrate and the chip lying outside the sealant free region, said applied sealant being of a sufficient viscosity and amount such that said sealant is precluded from flowing to the sealant free region so as to leave the array of microlocations free of sealant; and completing the cure of said sealant.

20. A method according to claim 19, wherein the electrically conductive interconnects are bumps.

21. A method according to claim 19, wherein the step of completing the cure of the sealant is done by heat treatment.

22. A method according to claim 19, wherein the sealant is applied to the interface between the chip and substrate by wicking.

23. A method for manufacturing a multicomponent flip-chip device for performing active biological operations, the device including a chip disposed adjacent to a substrate, the substrate including a via therethrough, wherein the device is adapted to receive a fluid to be placed on the substrate, and to flow through the via down to the chip, the method comprising the consecutively performed steps of:

placing a chip adjacent to a substrate;

applying a curable, wickable sealant to the interface between the substrate and the chip, said applied sealant being of a sufficient viscosity and amount such that said sealant is precluded from flowing to at least a portion of the chip bounded by the via; and completing the cure of said sealant by heat treatment.

24. A method for manufacturing a multicomponent flip-chip device for performing active biological operations, the device including a chip disposed adjacent to a substrate, the substrate including a via therethrough, wherein the device is adapted to receive a fluid to be placed on the substrate, and to flow through the via down to the chip, the method comprising the consecutively performed steps of:

placing a chip adjacent to a substrate;

wicking a curable, wickable sealant to the interface between the substrate and the chip, said sealant being of a sufficient viscosity and amount such that said sealant is precluded from flowing to at least a portion of the chip bounded by the via; and completing the cure of said sealant.

\* \* \* \* \*

UNITED STATES PATENT AND TRADEMARK OFFICE
CERTIFICATE OF CORRECTION

PATENT NO. : 6,254,827 B1
DATED : July 3, 2001
INVENTOR(S) : Ackley et al.

It is certified that error appears in the above-identified patent and that said Letters Patent is hereby corrected as shown below:

Title page,
Item [56], References Cited, U.S. PATENT DOCUMENTS,
For 4,584,075, please change to -- Goldstein et al. --
For 5,242,797, please change to -- Hirschfeld --.

OTHER PUBLICATIONS
For second "Drmanac et al." publication reference, please change "Hybridixation" to -- Hybridization -- and "Efficeint" to -- Efficient --.
Please change "Placek" to -- Palecek --
Please delete second reference to "Brown et al., "Electrochemically Induced Adsorption of Radio-Labelled DNA on Gold and HOPG Substrates for STM Investigation", *Ultramicroscopy*, 38 (1991) pp 253-264".
Please delete second reference to "Palacek, "New Trends in Electrochemical Analysis of Nucleic, Acids", *Bioelectrochemistry and Bioenergetics,* 20 (1988) pp 179-194".

Drawings,
Delete Drawing sheets, 7 and 8, and substitute therefor the drawing sheet, consisting of Figs. 6B, 7A & 7B, as shown on the attached pages.

Column 2,
Line 4, change "spring" to -- Spring --.
Line 23, change "sub-steps" to -- substeps --.

Column 3,
Line 41, change "D. Nanibhushan" to -- D. Dattagupta --.
Line 64, delete "#".

Column 5,
Line 8, change "array" to -- arrays --.

Column 6,
Line 64, change "It" to -- In --.

Column 7,
Line 35, change "effective" to -- effectively --.
Line 38, change "move" to -- moved --.
Line 47, change "a annular" to -- an annular --.

UNITED STATES PATENT AND TRADEMARK OFFICE
CERTIFICATE OF CORRECTION

PATENT NO. : 6,254,827 B1
DATED : July 3, 2001
INVENTOR(S) : Ackley et al.

It is certified that error appears in the above-identified patent and that said Letters Patent is hereby corrected as shown below:

Column 8,
Line 11, change "dispose" to -- disposed --.
Line 35, change "is flex" to -- is a flex --.
Line 51, change "light curable" to -- light-curable --.

Column 13,
Line 18, delete "20".
Line 33, change "utliized" to -- utilized --.

Column 14,
Line 3, change "concentration" to -- collection --
Line 47, change "burn-out" to -- burn out --.

Column 17,
Line 7, change "109" to -- 128 --.
Line 59, change "face" to -- surface --.

Column 18,
Line 14, change "light curable" to -- light-curable --.
Line 17, add "112" after "substrate".

Column 19,
Line 31, change "172" to -- 170 --.
Line 57, change "relative" to -- relatively --.

Column 20,
Line 10, change "illuminate" to -- illuminates --.
Line 35, change "on chip" to -- on-chip --.

Column 25,
Line 20, change "cite" to -- site --.
Line 49, change "342" to -- 352 --.

UNITED STATES PATENT AND TRADEMARK OFFICE
CERTIFICATE OF CORRECTION

PATENT NO. : 6,254,827 B1
DATED : July 3, 2001
INVENTOR(S) : Ackley et al.

It is certified that error appears in the above-identified patent and that said Letters Patent is hereby corrected as shown below:

Column 27,
Line 57, change "264" to -- 564 --.

Column 28,
Line 47, change "reaion" to -- region --.
Line 57, change "light curable" to -- light-curable --.

Column 29,
Line 32, change "curable" to -- light-curable --.

Column 30,
Line 9, change "light curable" to -- light-curable --.
Line 50, change "curable" to -- light-curable --.

Signed and Sealed this

Twenty-eighth Day of January, 2003

JAMES E. ROGAN
*Director of the United States Patent and Trademark Office*